(12) United States Patent
Kallury et al.

(10) Patent No.: US 7,468,281 B2
(45) Date of Patent: Dec. 23, 2008

(54) HOLLOW FIBER MEMBRANE SAMPLE PREPARATION DEVICES

(75) Inventors: Krishna Kallury, Torrance, CA (US); Joy Fan, Artesia, CA (US); Knut Rasmussen, Eiksmarka (NO); Stig Pedersen-Bjergaard, Oslo (NO)

(73) Assignee: Varian, Inc., Palo Alto, CA (US)

( * ) Notice: Subject to any disclaimer, the term of this patent is extended or adjusted under 35 U.S.C. 154(b) by 1017 days.

(21) Appl. No.: 10/475,896

(22) PCT Filed: Apr. 25, 2002

(86) PCT No.: PCT/US02/12952

§ 371 (c)(1),
(2), (4) Date: Apr. 6, 2004

(87) PCT Pub. No.: WO02/088672

PCT Pub. Date: Nov. 7, 2002

(65) Prior Publication Data

US 2004/0171169 A1   Sep. 2, 2004

Related U.S. Application Data

(60) Provisional application No. 60/287,158, filed on Apr. 26, 2001.

(51) Int. Cl.
| | | |
|---|---|---|
| *G01N 1/18* | (2006.01) | |
| *B01L 3/00* | (2006.01) | |
| *B01L 11/00* | (2006.01) | |
| *B01D 61/00* | (2006.01) | |
| *B01D 15/08* | (2006.01) | |
| *B01D 33/21* | (2006.01) | |

(52) U.S. Cl. .......................... 436/178; 422/61; 422/99; 422/101; 210/644; 210/649; 210/650; 210/500.23; 210/635

(58) Field of Classification Search ............ 422/61, 422/99, 101; 436/178; 210/644, 649, 650, 210/500.23, 635

See application file for complete search history.

(56) References Cited

U.S. PATENT DOCUMENTS 4,286,637 A * 9/1981 Wilson ....................... 141/374

(Continued)

FOREIGN PATENT DOCUMENTS

| GB | 2348380 | * | 10/2000 |
| WO | WO00/33050 | * | 6/2000 |

OTHER PUBLICATIONS

Book by LR. Snyder, JJ. Kirkland and JL. Glajch, entitled "Practical HPLC Method Development", published by John Wiley & Sons, Inc., 1997.

(Continued)

*Primary Examiner*—Walter D Griffin
*Assistant Examiner*—Lessanework Seifu
(74) *Attorney, Agent, or Firm*—Cynthia R. Moore; Bella Fishman

(57) ABSTRACT

Simultaneous sample purification, enrichment and analysis of pharmaceuticals, illicit drugs, pollutants, biotechnological products, synthetic organic reaction products and food/flavor ingredients from complex matrices can be performed using porous hollow fiber or porous-disk liquid-membrane devices. The devices are part of a multi-well (e.g. 96-well) plate. The devices can be used for selective separation and enrichment of complex mixtures containing trace levels of analytes, and can be used in tandem with analytical instruments which routinely handle multiple samples under high throughput screening conditions. A multi-well/multi-vial plate can into state-of-the-art HPLC or GC sampling systems or LC/MS or GC/MS instruments. Samples can be enriched several orders of magnitude and can directly be withdrawn from the fiber and injected into the chromatographic instruments. Alternatively, these enriched samples can be introduced directly into MS, CE or other detection devices. Selective extraction of complex mixtures of analytes can be achieved through variation of acceptor phase chemistry, liquid membrane coating, pore size control of the hollow fibers, nature of the polymer from which the hollow fibers are made or pH of the acceptor phase.

50 Claims, 20 Drawing Sheets

U.S. PATENT DOCUMENTS

| | | | |
|---|---|---|---|
| 5,229,004 | A | 7/1993 | Skelland |
| 5,252,220 | A | 10/1993 | Coughlin et al. |
| 5,512,180 | A | 4/1996 | Ho |
| 5,603,953 | A | 2/1997 | Herbig et al. |
| 5,650,323 | A * | 7/1997 | Root ................. 435/284.1 |
| 5,868,935 | A | 2/1999 | Sirkar et al. |
| 6,096,217 | A | 8/2000 | Kilambi et al. |
| 6,162,360 | A | 12/2000 | Ho et al. |
| 6,171,563 | B1 | 1/2001 | Ho |

OTHER PUBLICATIONS

Article by DN. Bailey and M. Keiner, entitled "Extraction of Acidic Drugs from Water and Plasma: Study of Recovery with Five Different Solvents", published by Journal of Analytical Toxicology, vol. 8, Jan./Feb. 1984, pp. 26-28.

Book by WL. McCabe and JC. Smith, entitled "Unit Operations of Chemical Engineering", published by McGraw-Hill, New York, 1976.

Book by JD. Seader and EJ. Henley, entitled "Separation Process Principles", published by John Wiley & Sons, Inc., 1998.

Book by JS. Fritz, entitled "Analytical Solid-Phase Extraction", published by John Wiley & Sons, Inc., 1999.

Book by EM Thurman and MS Mills, entitled "Solid-Phase Extraction", published by John Wiley & Sons, Inc., 1998.

Special Issue of Journal of Chromatography, vol. 885, Nos. 1 & 2, Jul. 14, 2000.

Article by SB Hawthorne, entitled "Analytical-Scale Supercritical Fluid Extraction", published by Analytiucal Chemistry, vol. 62, No. 11, Jun. 1, 1990, pp. 633A-642A.

Article by C. Arthur and J. Pawliszyn, entitled "Solid Phase Microextraction with Thermal Desorption Using Fused Silica Optical Fibers", published by Anal. Chem, 1990, vol. 62, pp. 2145-2148.

Article by NH Snow entitled "Solid-Phase Micro-Extraction of Drugs from Biological Matrices", published by Jounal of Chromatography A, vol. 885, (2000), pp. 445-455.

Book by T. Kumazawa, X. Lee, K. Sato, O. Suzuki, entitled "Applications of Solid Phase Microexraction", published by The Royal Society of Chemistry, London, 1999, pp. 470-485.

Article by C. Kroll and HH. Borchert, entitled "Solid Phas Microextraction (SPME) for Sample Preparation during Drug Metabolism Studies", published in Pharmazie, 53, (1998), 3, pp. 172-177.

Article by V. Loopez-Avila, R. Young and WF Beckert, entitled "Microwave-Assisted Extraction of Organic Compounds from Standard Reference Soils and Sediments", published by Anal. Chem., 1994, vol. 66, pp. 1097-1108.

Article by BE Richter, JL. Ezzell, D. Felix, KA. Roberts, and DW. Later, entitled "An Accelerated Solvent Extraction System for the Rapid Preparation of Environmental Organic Compounds in Soil", published by American Laboratory, Feb. 1995, pp. 24-28.

Book by CF. Poole and SK. Poole, entitled "Chromatography Today", published by Elsevier, Amsterdam, 1993.

Article by RE. Majors and KD Fogelman, entitled "The Integration of Automated Sample Preparation with Analysis in Gas Chromatography", published by American Laboratory, Feb. 1993, pp. 40W-40GG.

Article by T. Takeuchi and J. Haginaka, entitled "Separation and Sensing Based on Molecular Recognition Using Molecularly Imprinted Polymers", published by Journal of Chromatography B, 728, (1999), pp. 1-20.

Book entitled "Chemical Separations with Liquid Membranes", published ACS Symposium Series 642, American Chemical Society, Washington, DC., 1996.

Article by XZ. Wu, A. Hosaka, and T. Hobo entitled "An On-Line Electrophoretic Concentration Method for Capillary Electrophoresis of Proteins", published by Anal. Chem, 1998, vol. 70, pp. 2081-2084.

Article by R. Zhang and S. Hjerten entitled "A Micromethod for Concentration and Desalting Utilizing a Hollow Fiber, with Special Reference to Capillary Electrophoresis", published by Anal. Chem, 1997, vol. 69, pp. 1585-1592.

Article by JA. Jonsson and L. Mathiasson entitled "Liquid Membrane Extraction in Analytical Sample Preparation", published by Trends in Analytical Chemistry, vol. 18, No. 5, 1999, pp. 325-334.

Article by JA. Jonsson and L. Mathiasson entitled "Liquid Membrane Extraction in Analytical Sample Preparation", published by Trends in Analytical Chemistry, vol. 18, No. 5, 1999, pp. 318-325.

Article by E. Buyuktuncel, S. Bektas, O. Genc, and A. Denizli entitled "Poly(vinylalcohol) coated/Cibacron Blue F3GA-attached Polyprophylene Hollow Fiber Membranes for Removal of Cadmium Ions from Aquatic Systems", published by Reactive and Functional Polymers, 47, (2001), pp. 1-10.

Article by AK. Ghosh, V. Ramachandhran, MS. Hanra and BM. Misra, entitled "Synthesis, Characterization, and Performance of Nitrated Polysulfone Membranes", published by JMS, Pure Appl. Chem., A37(6), 2000, pp. 591-608.

Article by WJ. Koros and DG. Woods, entitled "Elevated Temperature Application of Polymer Hollow-Fiber Membranes", published by Journal of Membrane Science, 181, (2001), pp. 157-166.

Article by I. Masselin, X. Chasseray, L. Durand-Bourlier, JM. Laine, PY. Syzaret and D. Lemordant entitled "Effect of Sonication on Polymeric Membranes", published by Journal of Membrane Science, 181, (2001). pp. 213-220.

Article by Y Qin and J. Cabral, entitled "Theoretical Analysis on the Design of Hollow Fiber Modules and Modules Cascades for the Separation of Diluted Species", published by Journal of Membrane Science, 143, (1998), pp. 197-205.

Article by SA Gordeyev, GB Lees, IR Dunkin and SJ Shilton, entitled "Super-Selective Polysulfone Hollow Fiber Membranes for Gas Separation: Rheological Assessment of the Spinning Solution", published by Polymer, 42, (2001), pp. 4347-4352.

Article by AF Ismail, IR Dunkin, SL Gallivan and SJ Shilton, entitled "Production of Super Selective Polysulfone Hollow Fiber Membranes for Gas Separation", published by Polymer, 40, (1999) pp. 6499-6506.

Article by HG Ugland, M Krogh and KE Rasmussen entitled "Liquid-Phase Microextraction as a Sample Preparation Technique Prior to Capillary Gas Chromatographic-Determination of Benzodiazepines in Biological Matrices", published by Journal of Chromatography B, 749 (2000) pp. 85-92.

Article by KE Rasmussen, S Pedersen-Bjergaard, M Krogh, HG Ugland and T Gronhaug, entitled "Development of a Simple in-vial Liquid-Phase Microextraction Device for Drug Analysis Compatible with Capillary Gas Chromatography, Capillary Electrophoresis and High-Performance Liquid Chromatography", published by Journal of Chromatography A, 873 (2000) pp. 3-11.

* cited by examiner

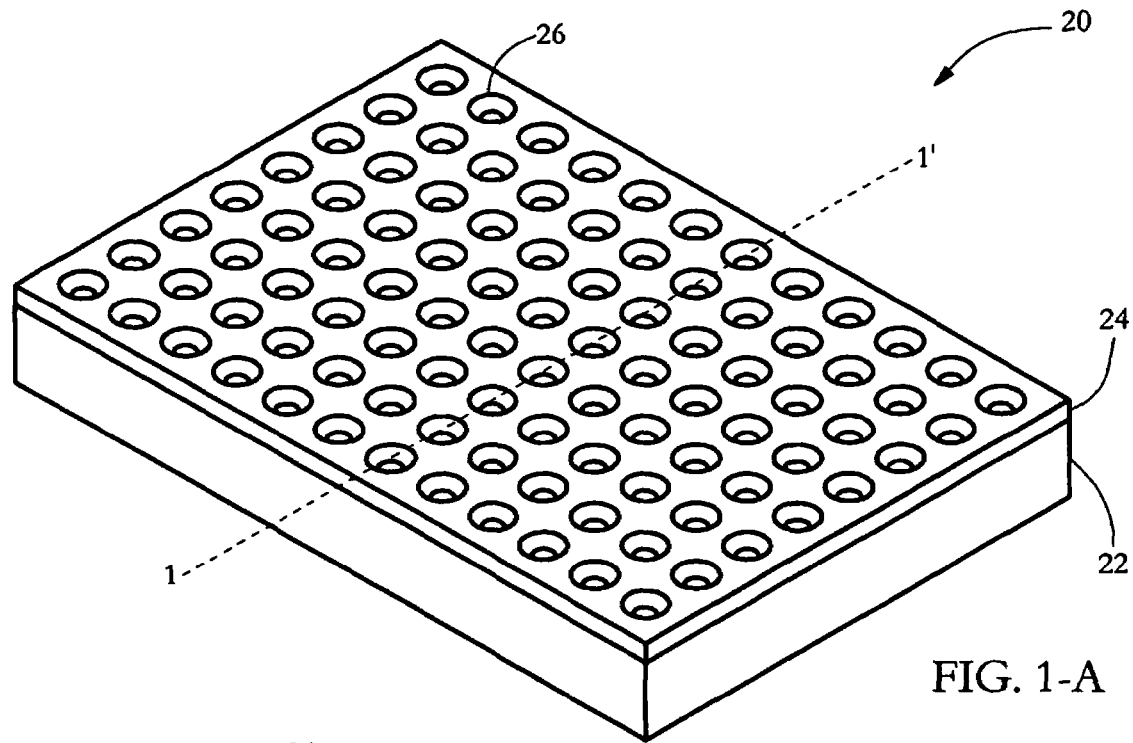
FIG. 1-A
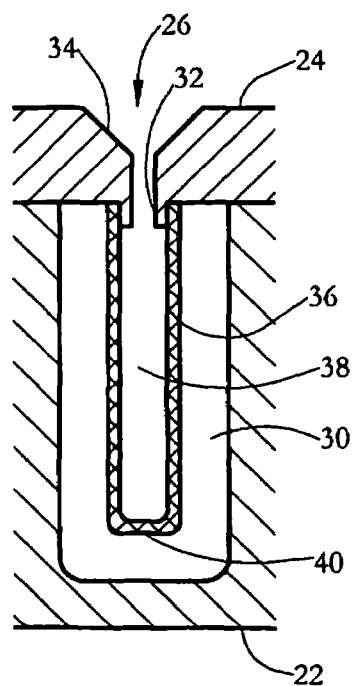
FIG. 1-B
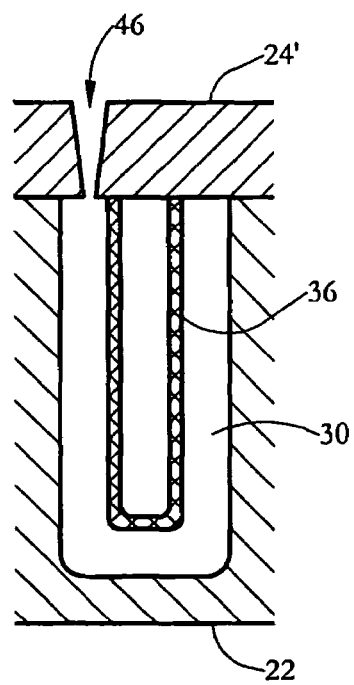
FIG. 1-C

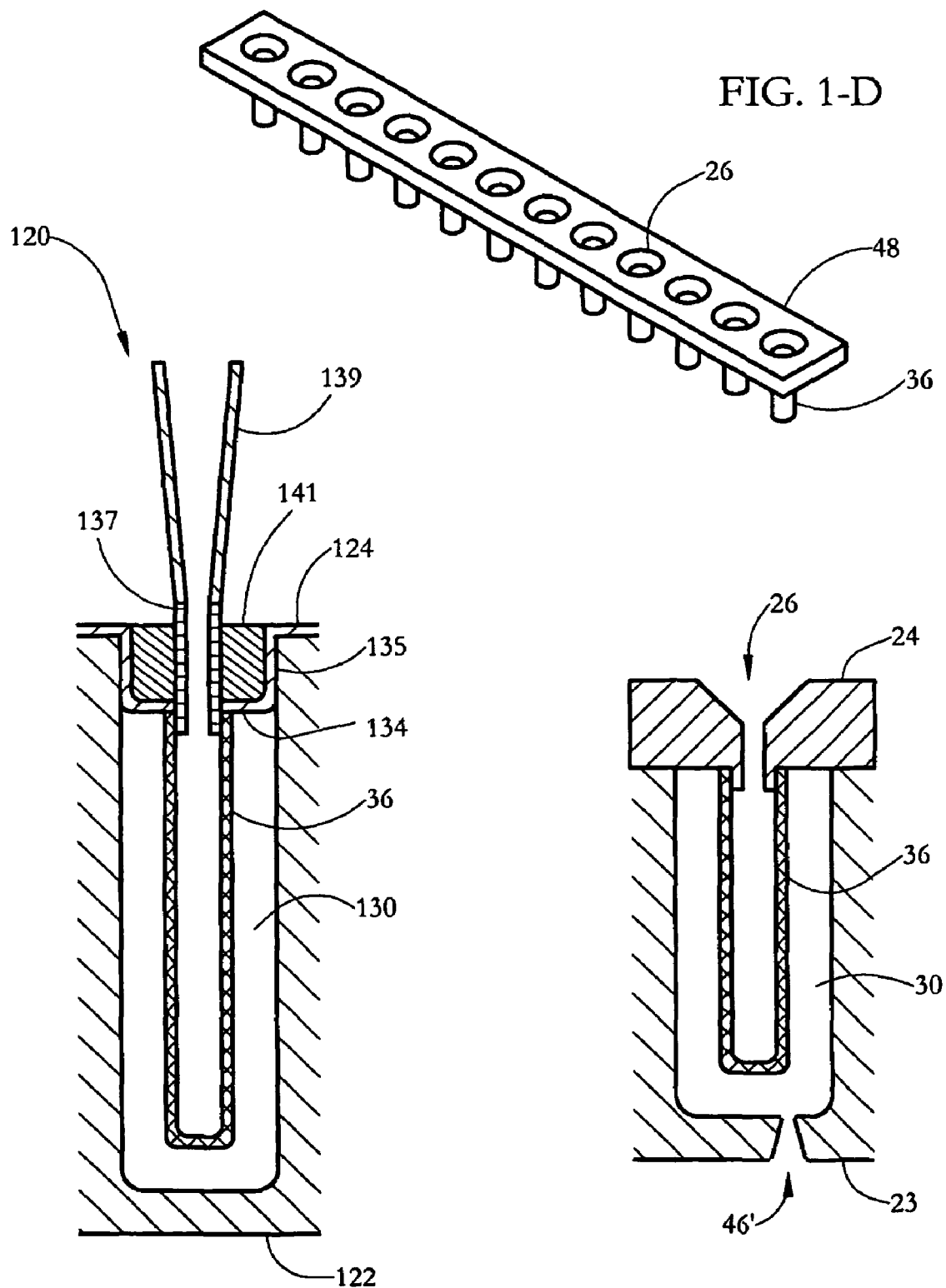
FIG. 1-D
FIG. 1-E
FIG. 1-F

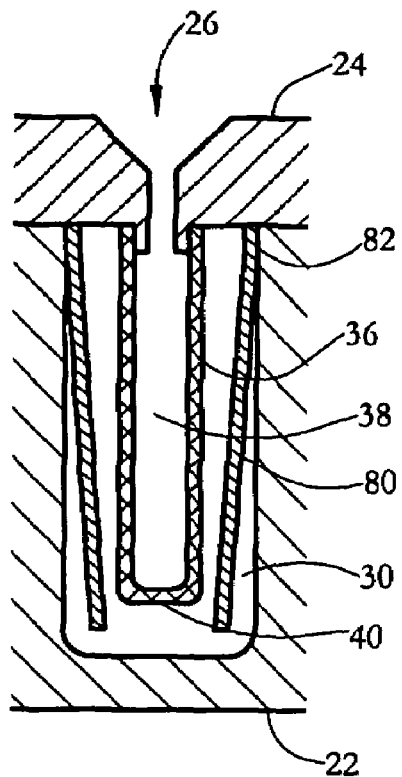
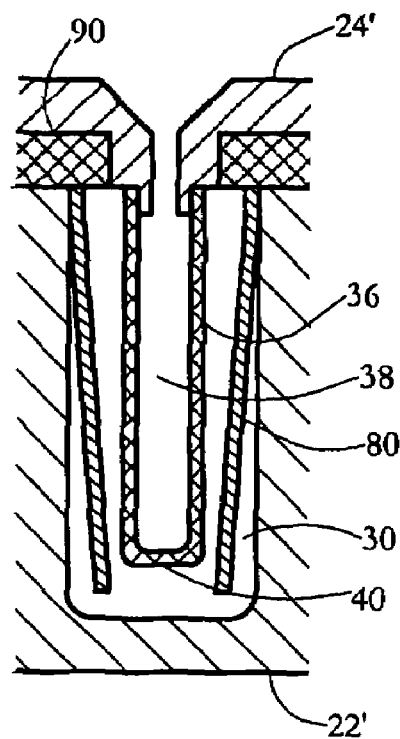
FIG. 2-A                FIG. 2-B
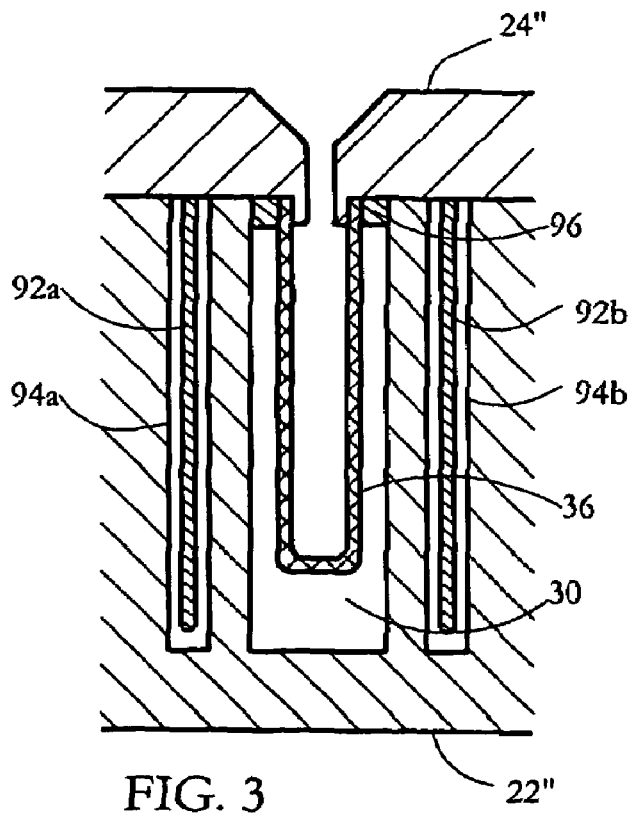
FIG. 3

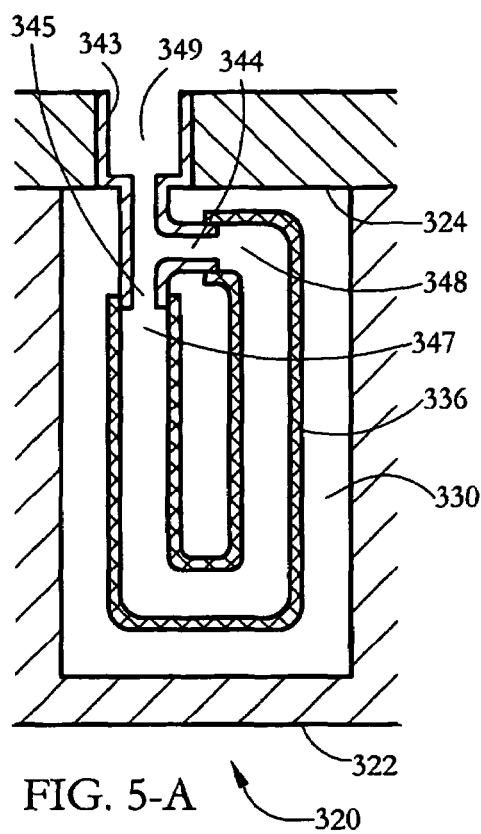
FIG. 5-A
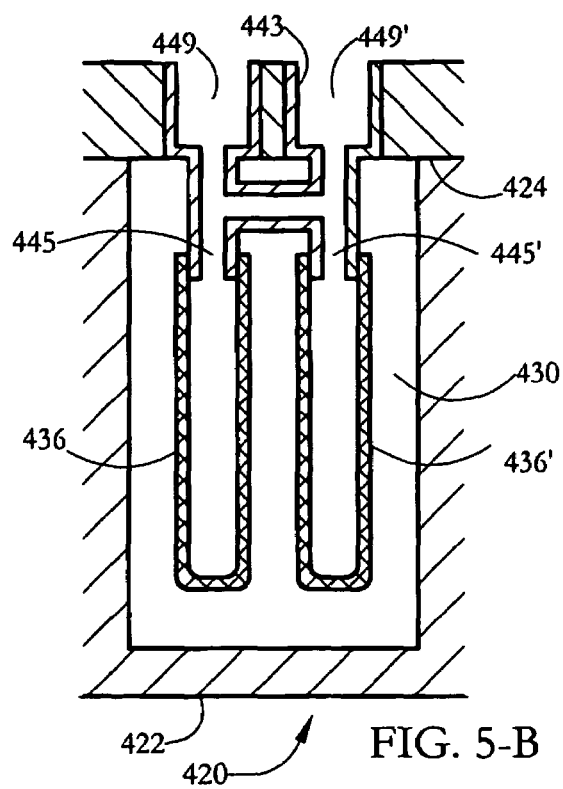
FIG. 5-B
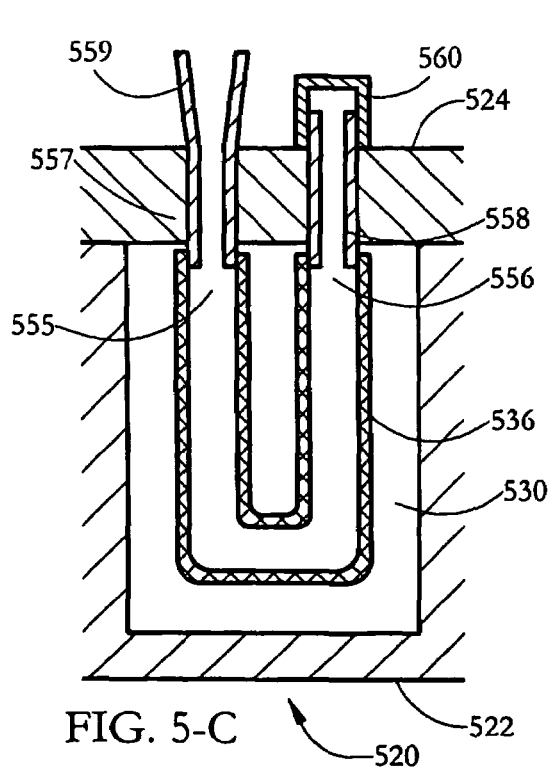
FIG. 5-C
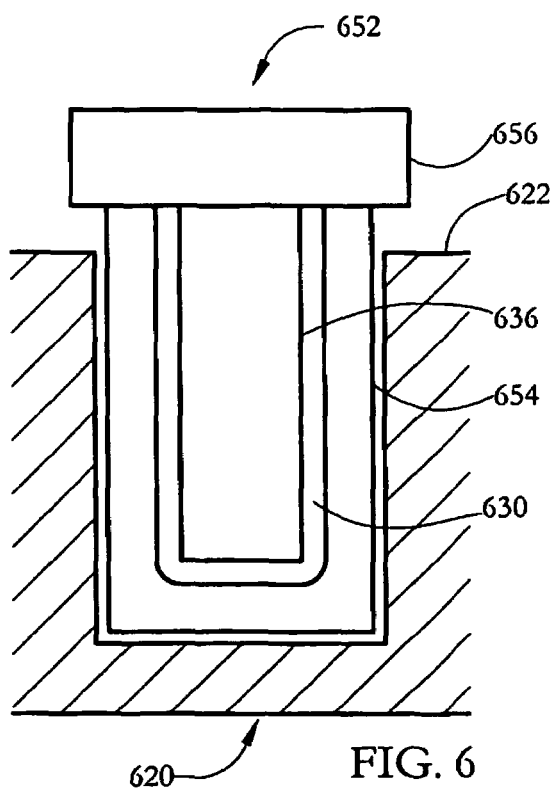
FIG. 6

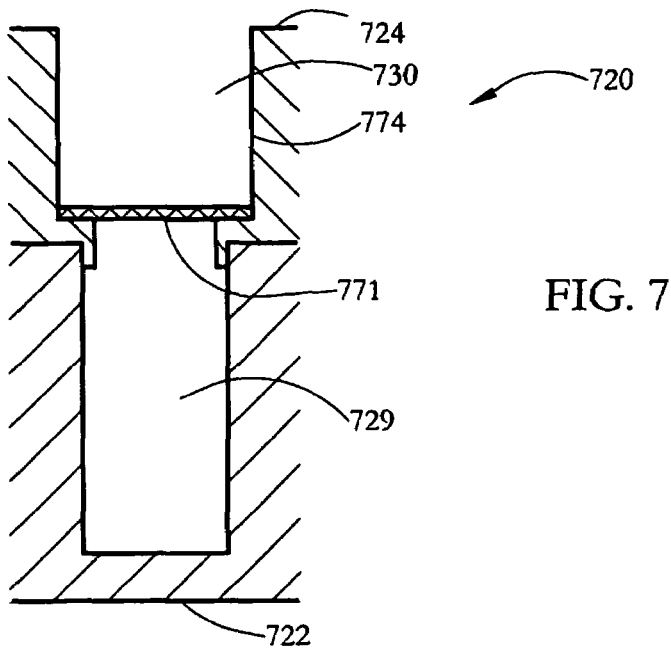
FIG. 7
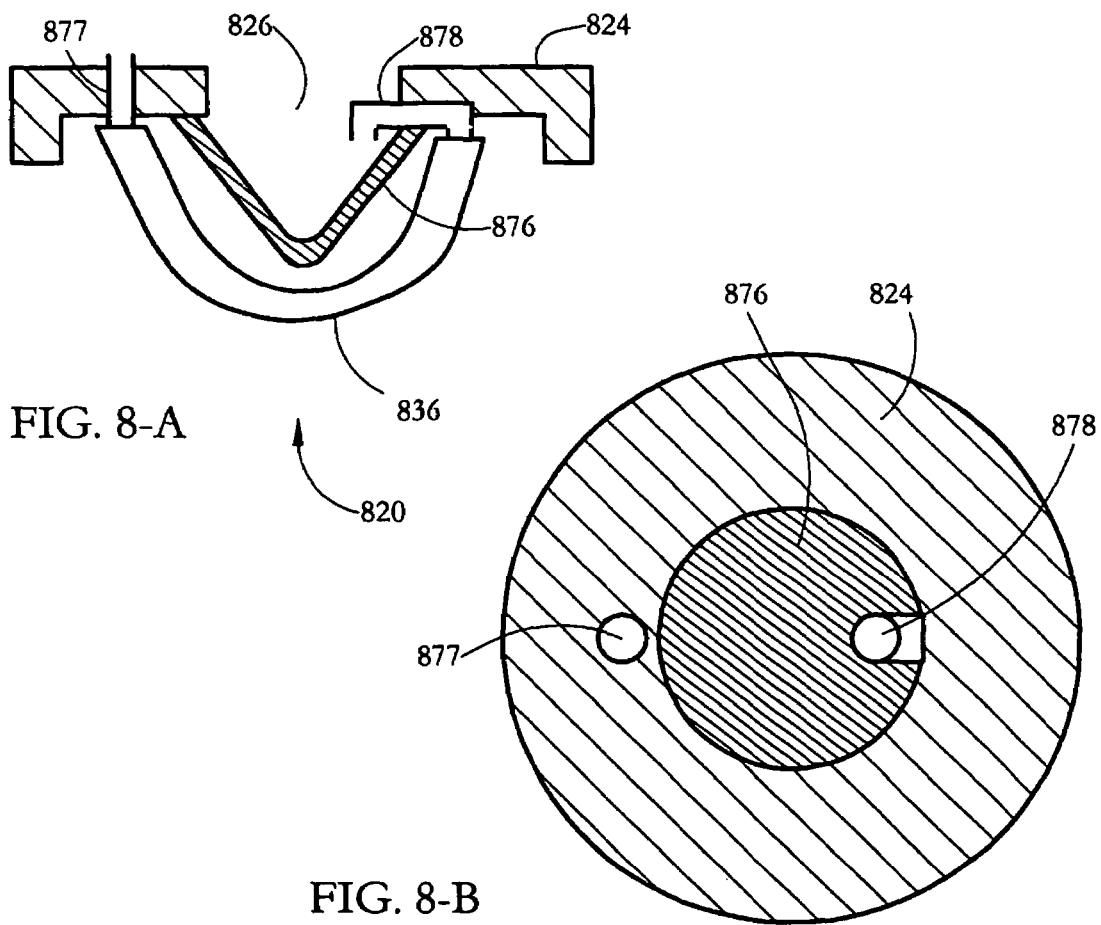
FIG. 8-A
FIG. 8-B

FIG. 13-A
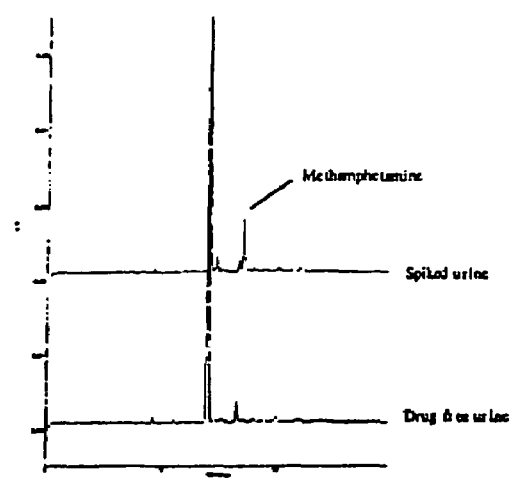
FIG. 13-B
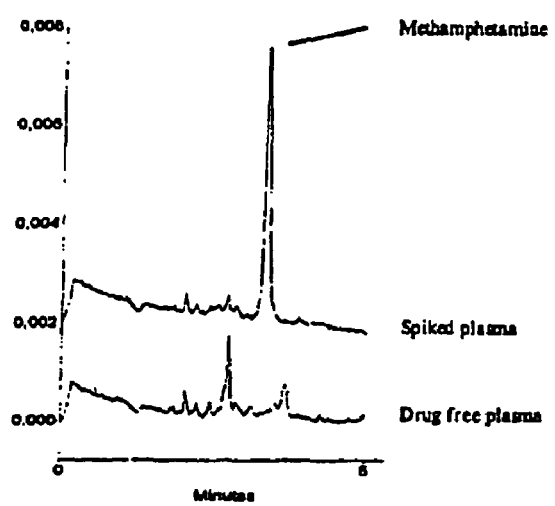
FIG. 14
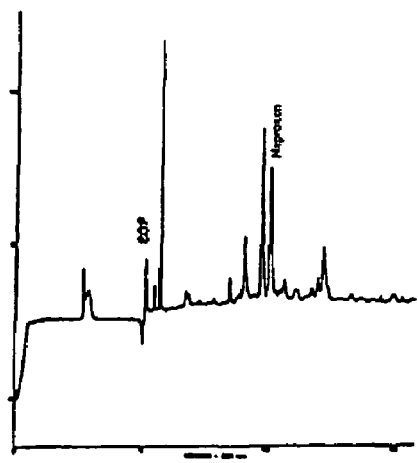

FIG. 15
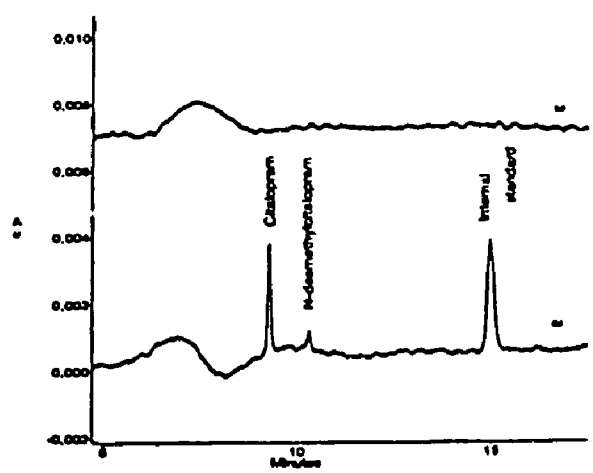
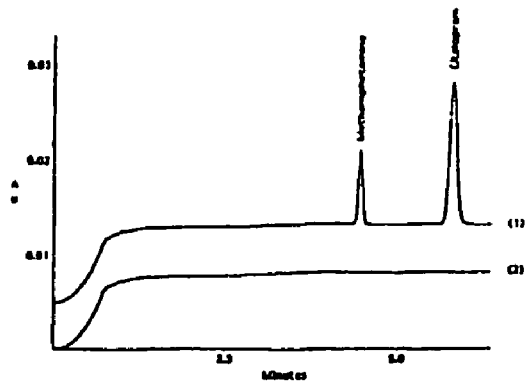
FIG. 16

FIG. 17
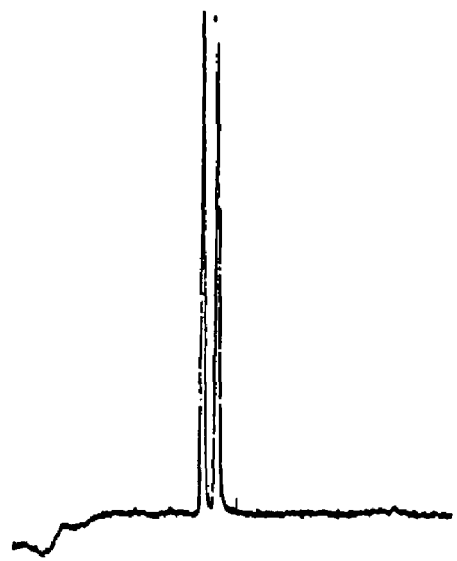
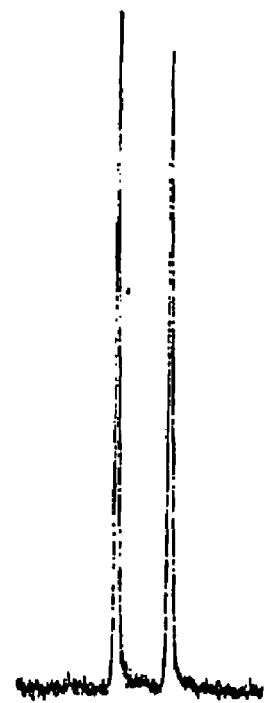
FIG. 18

FIG. 19-A
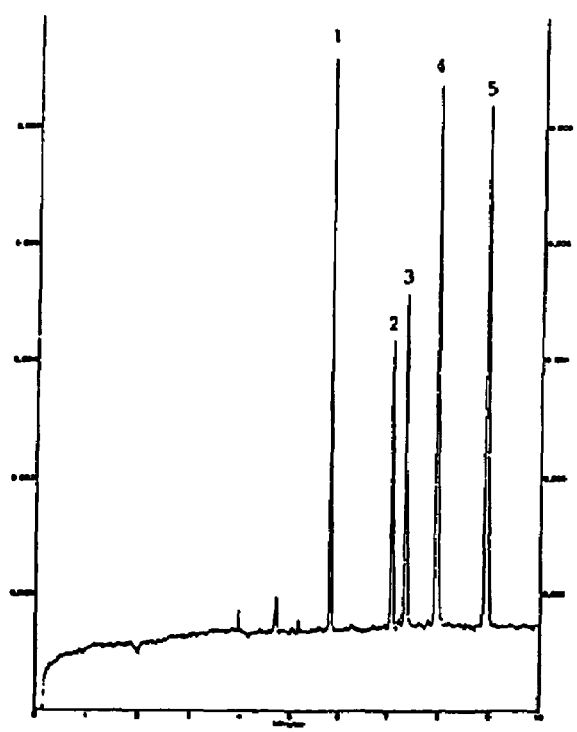
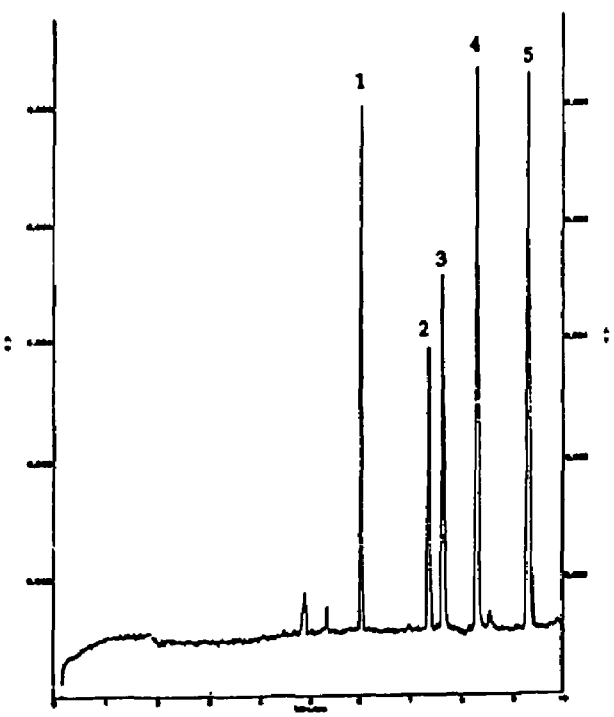
FIG. 19-B

FIG. 20
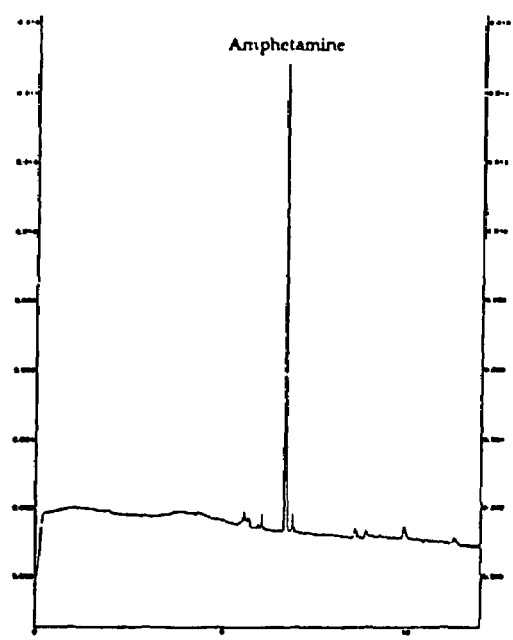
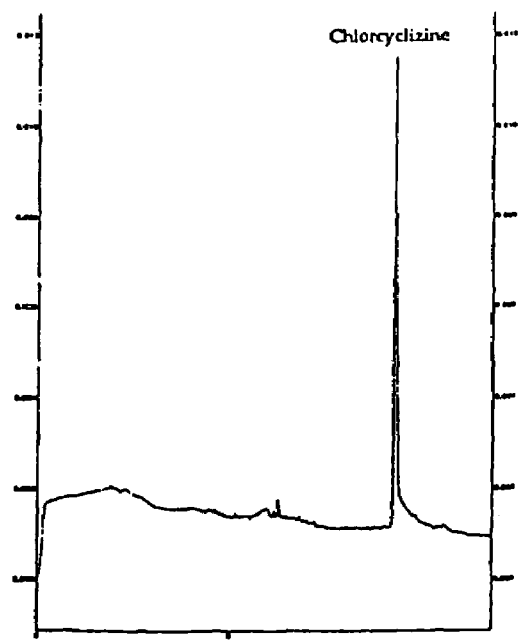
FIG. 21

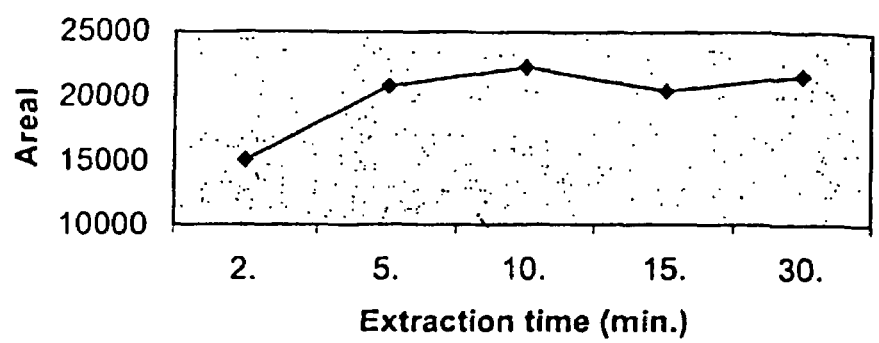
FIG. 22-A
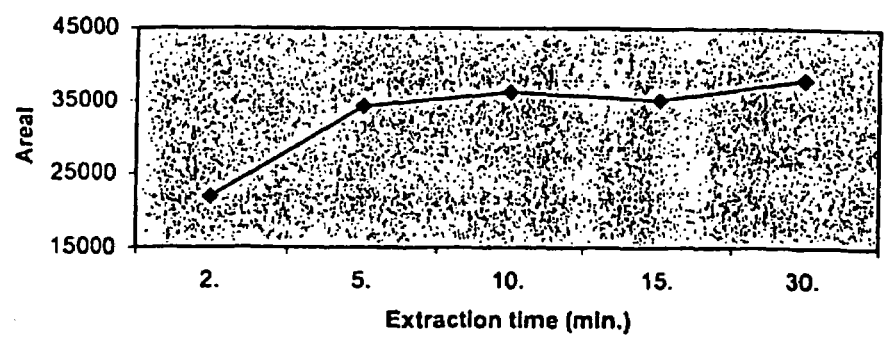
FIG. 22-B

FIG. 22-C
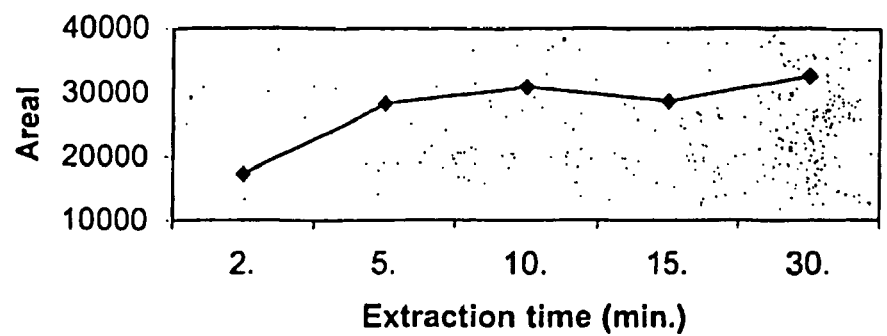
FIG. 22-D
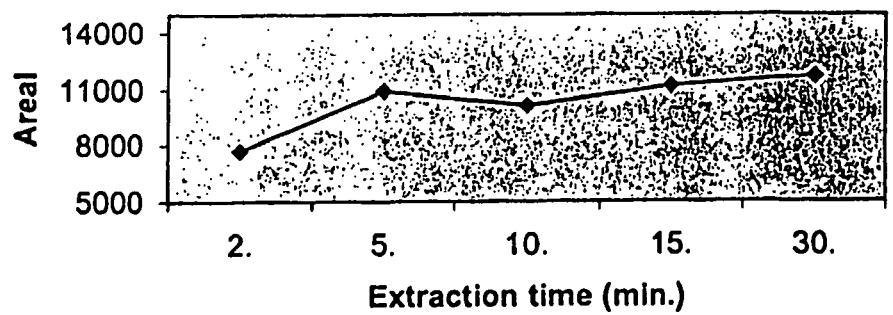

FIG. 22-E 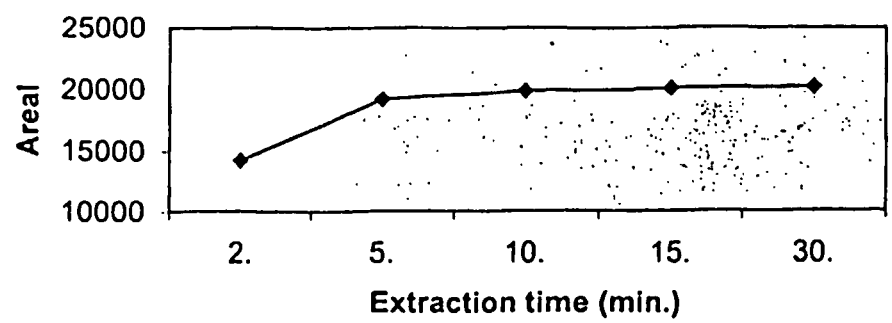
FIG. 22-F 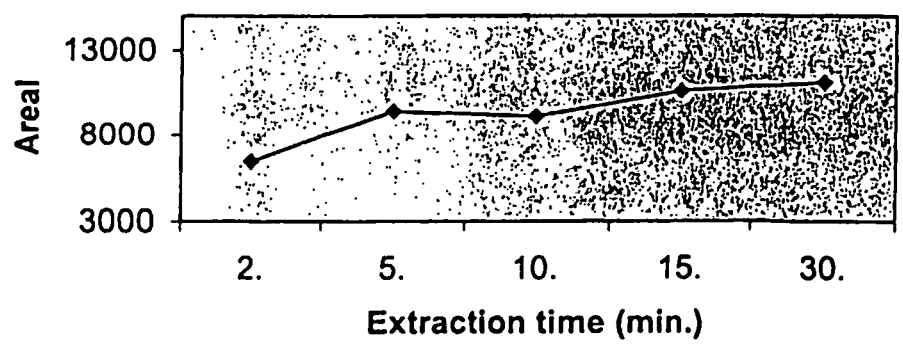

HOLLOW FIBER MEMBRANE SAMPLE PREPARATION DEVICES

RELATED APPLICATION DATA

This application claims the priority of U.S. Provisional Patent Application No. 60/287,158, filed Apr. 26, 2001, herein incorporated by reference.

FIELD OF THE INVENTION

The invention in general relates to preparing samples for chemical analysis or synthesis, and in particular to systems, methods, and compositions for performing simultaneous clean-up and enrichment of analytes of interest.

BACKGROUND OF THE INVENTION

Sample preparation, also termed pretreatment or clean up, is a pivotal step in analytical method development for pharmaceuticals, illicit drugs, food/flavor constituents, nutritional materials, environmental pollutants and agricultural products such as pesticides, herbicides, and insecticides. The scope of sample preparation is not restricted to these areas of chemical analysis, and can extend to a wide range of other fields of applicability such as synthetic chemistry, diagnostics and purification of biotechnological products. In the arena of pharmaceutical analysis, chromatography in general, and reversed phase high performance liquid chromatography (RP-HPLC) in particular, are extensively used for analyzing samples. Electrophoretic techniques have also gained recognition as viable analytical tools. In this context, sample preparation ideally provides a reproducible and homogeneous solution for injection into an analytical instrument such as a chromatography column. Ideally, sample preparation also serves to furnish a sample aliquot relatively free from interferences, prevents column damage, and is compatible with the intended analysis method. The precision and accuracy of the analysis method are frequently determined by the sample preparation procedure.

SUMMARY OF THE INVENTION

The present invention provides methods, devices, and kits for performing clean-up and enrichment of analytes of interest. A sample purification and enrichment method comprises: inserting a donor sample in a well of a multi-well plate, the donor sample comprising an analyte of interest; inserting a tubular hollow porous fiber into the well, the hollow fiber comprising a liquid extraction membrane, the hollow fiber enclosing an internal cavity separated from the donor sample by the extraction membrane; placing a static acceptor liquid in the internal cavity; simultaneously enriching and cleaning up the analyte of interest by extracting the analyte of interest from the donor sample, through the extraction membrane and into the acceptor liquid in the internal cavity, and transferring the analyte of interest and the acceptor liquid from the internal cavity to an analysis device.

A hollow-fiber membrane sample preparation multi-well plate for enriching and cleaning up samples comprises: a plurality of wells for holding a corresponding plurality of donor samples, each donor sample comprising an analyte of interest; and a plurality of porous hollow fibers situated in the corresponding plurality of wells, each hollow fiber being situated in one of the wells, each hollow fiber including a liquid extraction membrane enclosing an internal cavity of the hollow fiber, for holding a static acceptor liquid within each hollow fiber to receive the analyte of interest through the liquid extraction membrane into the acceptor liquid.

BRIEF DESCRIPTION OF THE DRAWINGS

The foregoing aspects and advantages of the present invention will become better understood upon reading the following detailed description and upon reference to the drawings where:

FIG. 1-A shows an isometric view of a sample preparation multi-well plate according to a presently preferred embodiment of the present invention.

FIG. 1-B shows a side sectional view of one of the wells and associated part of a top plate of the multi-well plate of FIG. 1-A.

FIG. 1-C is a side sectional diagram of a well and associated part of a top plate of an alternative multi-well plate, according to an embodiment of the present invention.

FIG. 1-D shows an isometric view of a top strip suitable for use with a well block such as the one shown in FIG. 1-A, according to an embodiment of the present invention.

FIGS. 1-E and 1-F show side sectional views of two wells and associated parts of top plates according to other embodiments of the present invention.

FIGS. 2-A and 2-B show side sectional views of two wells and associated parts of top plates according to other embodiments of the present invention.

FIG. 3 shows a side sectional view of a well and associated part of a top plate according to an embodiment of the present invention.

FIG. 4-B shows a side sectional view of one of the tubes of the assembly of FIG. 4-A.

FIG. 6 is a schematic illustration of a vial holding a hollow fiber, according to an embodiment of the present invention.

FIG. 7 shows a side view of a device including a disk-shaped membrane support according to an embodiment of the present invention.

FIGS. 8-A and 8-B show a side sectional view and a top view, respectively, of a vial cap or well cover including a collection container, according to an embodiment of the present invention.

FIG. 14 shows an electropherogram of naproxen after LPME extraction from human urine.

FIG. 15 shows an electropherogram of citalopram and its metabolite N-desmethylcitalopram from the plasma of a patient treated with citalopram after LPME of the plasma.

FIG. 16 shows an electropoherogram of methamphetamine and citalopram from human whole blood after LPME.

FIG. 17 shows an electropherogram of tramadol enantiomers after LPME from human plasma.

FIG. 18 shows an electropherogram of mianserine from the LPME of human plasma.

FIG. 19 shows an electropherogram of five basic drugs from human plasma and whole blood after LPME.

FIG. 20 shows an electropherogram of amphetamine from human urine after LPME.

FIG. 21 shows an electroopherogram of chlorcyclizine from human plasma after LPME.

FIGS. 22-A-F show extraction profiles of promethazine, methadone and haloperidol at different extraction times with 600 and 280 micron inner diameter polypropylene fibers, for two sets of experiments.

DETAILED DESCRIPTION OF THE INVENTION

Figure 4:
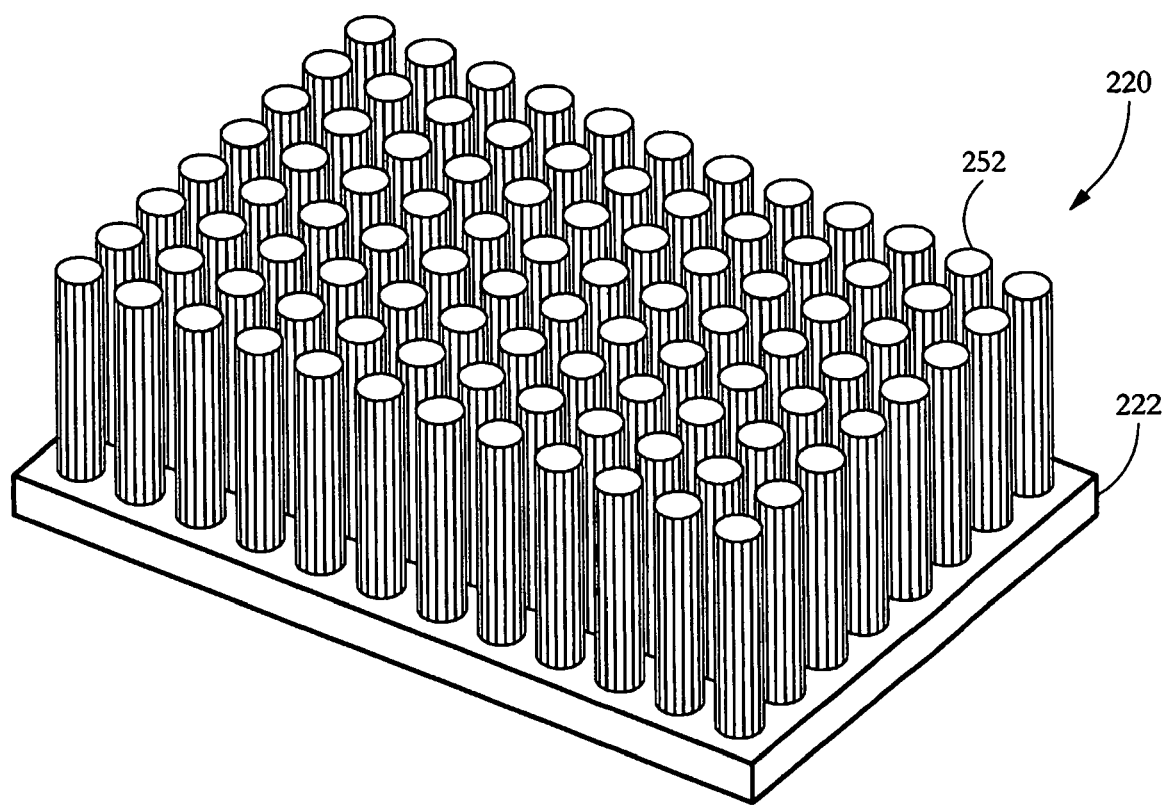
FIG. 4-A shows an isometric view of a sample preparation multi-well plate comprising a plurality of tubes individually mounted on a support block, according to an embodiment of the present invention.

In the following description, it is understood that each recited element or structure (e.g. plate) can be formed by or be part of a monolithic structure, or be formed from multiple distinct structures. The statement that a sample or liquid is static in a well is understood to mean that the sample does not flow through the well. A static sample may be subjected to agitation or vibration. The following description illustrates embodiments of the invention by way of example and not necessarily by way of limitation.

Sample matrices consist of products of organic, biological or inorganic origin, and can exist in the form of solids, semi-solids (including creams, gels, suspensions and colloids), liquids and gases. To cater to the present generation requirements of trace level analysis and high throughput screening, which involves several thousands of samples at a time, different device formats and sample preparation techniques have been developed, and are frequently automated. Such techniques include liquid-liquid extraction, solid phase extraction, and supercritical fluid extraction. Recent advances in these extraction methods include solid phase microextraction, microwave-assisted solvent extraction, accelerated solvent extraction, derivatization protocols, liquid-liquid microextraction, and methods using molecularly imprinted polymers.

Liquid-liquid extraction (LLE) offers the benefits of quantitative recovery, availability of a wide selection of solvents or combinations of solvents, easier sample concentration after extraction, and high purity that minimizes sample contamination. Liquid-liquid extraction may lead to emulsion formation, and may require time-consuming multiple extractions if the distribution constant between the organic and aqueous phases is low. Apart from miscibility considerations, an important criterion for solvent selection in liquid-liquid extraction is polarity. A variant of liquid-liquid extraction is micro-extraction, where an organic solvent of density less than that of water is employed. Modern autosamplers are capable of performing such micro-extractions automatically on small volumes of aqueous samples in 2 mL vials.

Solid phase extraction (SPE) is currently one of the most popular methods of sample pretreatment for pharmaceutical analysis. Unlike LLE, which is a one-stage separation process, SPE is a chromatographic procedure resembling HPLC. SPE protocols normally consist of four steps: conditioning the packing, sample application, washing the packing to remove interferences, and recovery of the analytes of interest with more concentrated solvent. SPE devices encompass several formats, such as catridge, disk and 48/96 deep well plates. Compared to LLE, SPE can allow more complete extraction of analytes, more efficient separation of interferences from analytes, reduced organic solvent consumption, easier collection of total analyte fraction, more convenient manual operation, removal of particulates and easier automation. On the other hand, SPE may be affected by variability of the bonded phases used in SPE catridges, irreversible adsorption of some analytes, and leaching of either impurities present in the sorbents or of the bonded phases themselves. Irreversible adsorption of analytes can drastically lower recovery, while leaching can lead to contamination of the sample solutions. With silica-based sorbents, an additional consideration is the passage of fines through the frits used in the SPE catridges. SPE catridges are normally meant for one time use only. Using SPE, samples are normally preconcentrated by a factor of 2 to 4 only. For additional enrichment, further evaporation of solvent is typically necessary.

Solid phase microextraction (SPME) is an offshoot of SPE. A typical SPME method employs devices consisting of a fine, solid fused silica fiber coated with a polymeric stationary phase. The fiber is dipped into the solution to be analyzed, and analytes diffuse to and partition into the coating as a function of their distribution coefficients. Different coatings are commercially available for SPME-GC. Examples of commercially-available relatively less polar coatings include polydimethylsiloxane (PDMS), and PDMS containing divinylbenzene (PDMS-DVB). Exemplary commercially-available, relatively more polar coatings include polyacrylates (PA). Carbowax-DVB and carboxen-PDMS fibers have also been introduced recently. SPME is predominantly employed in environmental analysis in tandem with GC detectors. In SPME, the nature of the partition process is different from SPE or HPLC, and the choice of fiber can be limited. Moreover, quantitation can be difficult when several compounds are involved in competition in an unknown sample matrix.

The selective transfer of analytes or unwanted interferences across a membrane can be used to separate analytes of interest. Membranes used in separation technology can be made from synthetic organic polymers, cellulose derivatives, or glass fibers, among others. Filtration and solid-phase extraction disks represented the major areas of applications for membranes in sample preparation until recently.

Analytes can be moved across membranes by diffusion as a result of chemical or electrochemical gradients. Ultrafiltration, reverse osmosis, dialysis, microdialysis and electrodialysis are examples of techniques that utilize membranes for concentration, purification and separation of analytes. Membranes can be produced in many forms, such as sheet, roll, disk, capsule, cartridge, spiral-wound and hollow fibers. Semi-permeable membranes allow passage of certain compounds, but not others, as in a flowing dialysis system.

Microporous semi-permeable membranes permit selective filtration according to the size of their micropores. For example, molecular weight cutoff membranes allow passage of small molecules such as drugs, while precluding passage of large molecules such as proteins. Porous electrically charged or ion-exchange membranes have pore walls with fixed positive or negative charges. The passage of ionic molecules across the membrane is governed by pore size and membrane charge. In dialysis with semi-permeable membranes, the sample (donor) solution is placed on one side of the membrane and the acceptor solution is on the other side of the membrane. In some cases, interferences diffuse through the membrane, leaving a purified donor solution. More often, the analyte(s) of interest pass through the membrane into the acceptor solution, leaving interferences in the donor solution. For RP-HPLC analysis, both the donor and acceptor liquids are usually water or buffer.

Dialysis in a flowing system has also proved effective as an on-line sample preparation technique for the deproteination of biological samples before HPLC analysis. The acceptor solvent is pumped to a trace enrichment column, which is later back-flushed into the HPLC instrument. These techniques have been automated and are in routine use in laboratories.

Typical advantages of membrane-based systems developed to date over other sample preparation techniques include (a) reduced risk of overloading with sample or matrix components, (b) reduced contamination and exposure to toxic or dangerous samples through the use of closed flow systems, (c) minimal use of organic solvents, and (d) easy automation in flow systems. At the same time, membranes can be subject to fouling by particulates or macromolecules. Such fouling can result in flow rate decreases and diminished membrane effectiveness.

Sample Preparation Using Supported Liquid Membranes (SLM):

Supported-liquid membrane (SLM) enrichment techniques can be thought of as combining aspects of dialysis and liquid-liquid extraction. In one implementation, a porous membrane support is impregnated with a water-insoluble organic solvent and is placed in a mounting block. Compounds are extracted from the donor side into the membrane as a function of their solubility in the supported liquid, where they are then re-extracted from the membrane into the acceptor side. A simple example of the use of this technique is the enrichment of a carboxylic acid from an aqueous donor solution. By adjusting the pH of the donor solution below the $pK_a$ value of the acid, the ionization of the carboxylic acid is suppressed, allowing the nonionic form to be extracted into the immobilized liquid on the membrane. The non-ionized acid diffuses through the membrane to the acceptor side, which has a basic pH where the organic acid is extracted in its ionized form. Therefore, the carboxylate anion is concentrated since it no longer can reextract into the membrane. Enrichment factors of several hundred can be achieved using a support liquid membrane sample preparation method of the present invention, as described in the Examples below. Placing a sorbent trap or precolumn between the membrane device and the HPLC instrument allows the analyte to be concentrated ever further.

Sample separation and enrichment using supported liquid membranes on porous hollow fiber supports employ a porous hollow fiber or combination of several fibers, a liquid membrane supported in the pores of the fiber, a sample enriching acceptor solvent/solution, and a device format for introducing the sample and acceptor solutions into different regions of the fiber. The device format enables partitioning and enrichment of the analyte under investigation, and transfer of the analyte-enriched acceptor solution into an analytical instrument for quantitation.

Microporous supports useful for incorporating membrane forming solid or liquid materials are known in the art. A hydrophobic microporous support is a material that is not spontaneously wetted by water and has an open-celled, interconnected structure. Such a microporous support should be composed of materials that are compatible with the solid or liquid membrane substance used for coating. Examples of materials suitable for such supports include polyolefins, polysulfones, polytetrafluoroethylene, polycarbonates, polyetherketones, polystyrene, cellulose, cellulose acetate and other polymeric materials. The pores of commercially available microporous materials are in the range of about 0.02 to about 2 microns in effective diameter. Pores as small as 0.01 micron and as large as 10 microns are not unusual and a specific pore size is not necessarily important in a given application. Typically, commercial porous support thickness values range between 10 and 300 microns, although thicker supports are used for certain applications. The porosity of supports is ideally sufficient to provide an open network through the support. Typical commercial fibers have a porosity of about 30 to 80%. A commercially-available Celgard® polypropylene membrane, for example, has a porosity between 40 and 50%. Porosity is defined as the fractional volume of the membrane that is open rather than substrate material. Supports may be treated to alter their surface properties. For example, polyethylene films may be treated with chromic acid to render the films less hydrophobic. Hollow fiber format of supports (in comparison with a flat sheet), especially in helical or spirally wound formats, provide a high ratio of support surface area to volume of the sample solution and acceptor solution.

For aqueous sample solutions, the supported liquid membrane is typically a water immiscible organic solvent. When a sample solution consists of analytes dissolved in organic solvent, the membrane is typically an aqueous-based system. Since sample pretreatment predominantly involves aqueous solutions, the supported membranes are typically chosen from aliphatic or aromatic hydrocarbons, ethers, nitrites, aldehydes or ketones, and alcohols which are immiscible with water. Some specific suitable membrane liquids include 1-octanol, 2-octanone, diphenyl ether, nitrophenylalkylethers ranging from pentyl to decyl for the alkyl part, higher alkylpyridines such as 4-(1-butylpentyl) pyridine, 1-octyl-2-pyrrolidone, benzonitrile, diisopropylbenzene, cyclohexanone, tri-n-butylphosphate, triglycerides with alkyl chain lengths of 6 to 24 carbon atoms and fatty acid esters of cholesterol with alkyl chain lengths of 2 to 20 carbon atoms, to mention a few examples. Membrane stability tends to improve when an extremely hydrophobic liquid such as dodecane is used, but very little flux is produced owing to low diffusion coefficients in such liquids. On the other hand, polar solvents tend to afford high diffusion coefficients, but have low stability. To balance these factors, it is desirable to use a mixture of solvents. Most membranes have lifetimes of five days or less. With nitrophenyloctyl ether, membrane lifetimes of 10-20 days have been observed. Suitable surfactants may also be used to enhance the stability of mixed solvent membranes, as for example, nonionic surfactants with hydrophilic-lipophilic balance ranging from 8 to 15, such as polyoxyalkylene esters or ethers.

Polymeric membranes formed either by polymerization of monomers in the pores of support materials, or by coating preformed polymers dissolved in appropriate solvents, have been found to be significantly more stable and also exhibit high partition coefficients towards small organic molecules. Examples of such polymers include polyalkylene glycols, polyvinylpyrrolidones, polyesters, polyurethanes and functionalized polyolefins. Polydimethylsiloxane membranes were reported to demonstrate selectivity for higher alcohols compared to ethanol.

The acceptor liquid contacts the outer shell surface of a hollow fiber membrane when the sample solution is passed through the lumen side of the fiber. Conversely, if the sample solution is circulated through the shell side, the acceptor solution is passed through the lumen side. Acceptor solutions can be aqueous, basic, or acidic solutions, or polymers in the liquid state such as polyethylene glycol, depending on the type of application. Acceptor solutions can also include complexing agents capable of forming a complex with the analyte(s) of interest.

Several flow-through systems employing liquid membranes supported on hollow fiber supports have been described. Commonly, provision is made for sample (feed) flow from the shell side of the fibers, as well as for acceptor solution (strip solution) flow across the lumen side of the fiber, both involving pumping systems. For information on known hollow fiber systems see for example U.S. Pat. Nos. 4,666,543, 5,282,964, 5,474,902, 5,846,427, 5,202,023, and 5,252,220.

According to the preferred embodiment of the present invention, sample preparation systems and methods can employ a variety of sampling device formats incorporating supported liquid membranes contained in the pores of polymeric hollow fibers. Such devices are capable of simultaneously effecting clean up and enrichment from trace/impure state of a sample to several orders of magnitude more concentrated and purified condition. In particular, such devices are capable of providing microliter level volumes of pure extracts, which are not commonly obtainable directly by standard sample preparation techniques. Furthermore, these devices are amenable for integration into state-of-the-art automated chromatographic and mass spectrometric instrumentation used for high throughput screening of pharmaceuticals and other types of analytes. High-throughput screening involves the automated analysis of large numbers of samples within short time frames. Samples can be purified and enriched directly on the autosampler systems of these analytical instruments, and aliquots from these enriched and purified sample solutions can be injected directly into the chromatographic columns or mass spectrometer.

According to the preferred embodiment of the present invention, the sampling device formats comprise 48 or 96 or 384 well plate blocks carrying hollow fibers suspended in each well. Extraction/purification can be carried out by automatic or manual delivery of sample solutions into the shell side of the fibers in each well. The fibers carry the acceptor (or strip or extracting) solution on the lumen side and analytes diffuse through the supported liquid membrane in the pores of the fibers into the acceptor solution. The autosampler injector needle of the chromatographic instrument can pick up the enriched sample directly from the fiber and deliver it to the instrument for analysis. The well plate assembly can be mounted directly onto the analytical instrument.

Alternatively, the sample enrichment process can be carried out in autosampler vials, which are commonly used in liquid chromatographic instruments. A miniature device can incorporate hollow fibers into each of the vials individually. The ends of these fibers can be connected to appropriate inlet/outlet ports located in the cap portion of the vials for automated delivery and withdrawal of acceptor solution before and after enrichment, respectively. Thus, the devices provide for enriching and analyzing multiple samples at a time through an automated sampling system.

The fibers suspended in the well plates may be modified by several permutations and combinations of parameters to incorporate selectivity features which would permit the isolation of a single analyte from a complex mixture or a group of analytes from other groups or exclude unwanted materials from human fluids or synthetic reaction mixtures. Thus, fibers made from different polymeric materials (such as polypropylene, polysulfone, polycarbonate or polyether sulfone, etc.) can be suspended in the wells to harness selectivity arising from fiber chemistry. Alternatively, the fibers can be coated with different membrane forming liquids to utilize membrane-based selectivity for optimization of enrichment and selective extraction. The chemistry of the acceptor solutions (strong or weak acids or bases, for example) as well as the pH of the acceptor solutions can be varied along with variation of the fiber chemistry, to achieve the desired separation. Furthermore, the pore size of the fibers can also be varied to effect selective diffusion into the fiber.

With a multiwell format, all these variables can be incorporated into one and the same well plate block. This feature enables the probing of several selectivity-imparting parameters simultaneously to arrive at optimal conditions for a desired separation/purification. Making use of a host of acidic, basic and neutral pharmaceuticals in wide circulation around the world, the performance of the device is demonstrated with respect to enrichment, selective extraction and speed of analysis of multiple samples.

The devices of the present invention operate in the static mode. Sample solution to acceptor liquid ratios ranging from 20 to 200 can be employed. Thus, one has the choice of using sample solution volumes as low as 500 µL to as much as 10 mL. Furthermore, the extractions can be completed in about 15 minutes and sample enrichments ranging from 30 to 200 fold can be achieved. Such high levels of sample enrichment are not commonly achievable with presently-available standard sample preparation techniques.

Systems and methods according to the preferred embodiment of the present invention address shortcomings of state-of-the-art sample preparation techniques such as liquid-liquid extraction, solid phase extraction and solid phase micro-extraction. These techniques may not easily handle very small volumes of solvents, e.g. less than 100 microliters of solvent used as extracting medium. Analysts may prefer to use such small volumes during sample preparation in order to achieve a high degree of sample enrichment, while effecting complete extraction simultaneously. Typically, these techniques use larger volumes of sample. A subsequent concentration and/or reconstitution step is then used to generate detectable sample levels for analysis. In a number of instances, extraction is incomplete when these techniques are used, which leads to problems in quantitation.

Membrane-based separations or extractions are particularly attractive since these approaches can use small volumes of solvents and can withstand extremes of pH, unlike silica-based solid phase extraction systems. Polymeric materials used in solid phase extraction, such as Oasis®, can overcome this pH problem, but may not exhibit a wide spectrum of selectivity and are not universal with respect to solvent compatibility. In the prior art, both silica and polymer based solid phase extraction systems are available in the well plate format and have been used for sample purification during high throughput screening of pharmaceuticals. However, problems such as contamination due to leaching from the sorbents and strong retention of analytes (sometimes irreversible retention) can persist.

According to the preferred embodiment of the present invention, hollow fiber membranes can be used as devices for obtaining sample enrichment of several orders of magnitude, both with small organic molecules and with complex biomolecules such as proteins and nucleic acids. Fibers of different chemistries or different acceptor solutions or different liquid membranes can be employed in one and the same device format. A wide spectrum of selectivity can be achieved by employing different fiber/membrane chemistries and variation of acceptor phases or pH simultaneously.

Simple supported liquid membrane hollow fiber devices can be employed in the well plate and autosampler vial formats in a static mode that can furnish a high degree of sample enrichment. The devices can be operated interchangeably either in the manual or automated modes and provide rapid screening of large volumes of samples. These devices can function as either two-phase extraction systems (aqueous feed solution on the shell side of the fiber and organic solvent acceptor solution on the lumen side, with the same solvent forming the supported membrane) or as three phase extraction systems (aqueous feed, supported liquid membrane phase and an aqueous acceptor phase) during the sample enrichment process.

Theory:

The theoretical discussion below is intended to generally illustrate particular embodiments of the present invention, and is not intended to limit the scope of the invention to the described illustration.

Consider a hollow fiber membrane, two-phase liquid phase micro-extraction (LPME) system having donor and acceptor phases, with the supported liquid membrane being the same material as the acceptor. When an analyte attains concentration equilibrium between the two phases (see equation 1), extraction is complete. For an analyte A, the distribution between the two phases is governed by Nernst's distribution law, as given in equation 2.

$$A(donor) \leftrightarrows A(acceptor) \quad (1)$$

$$K_{a/d} = C_{eq[a]}/C_{eq[d]} \quad (2)$$

In eq. [2], $C_{eq[a]}$ is the equilibrium concentration of A in the acceptor phase and $C_{eq[d]}$ is the concentration of A in the donor phase. By the law of conservation of mass, the initial mass of the analyte ($n_i$) is equal to the sum of the individual quantities of the analyte present in the two phases, as in equation 3.

$$n_i = n_d + n_a \quad (3)$$

At equilibrium, eq. 3 can also be written as $$C_i V_d = C_{eq[d]} V_d + C_{eq[a]} V_a \quad (4)$$

where $C_i$ is the initial concentration and $V_d$ and $V_a$ are the sample phase volume and acceptor phase volume, respectively. The amount of analyte extracted into the acceptor phase of the system can be calculated by substituting $K_{a/d} C_{eq[d]}$ for $C_{eq[a]}$ in equation 3.

$$n_{eq} = K_{a/d} V_a C_i V_d / (K_{a/d} V_a + V_d) \quad (5)$$

Then, the recovery (R) can be expressed by equation 6 below, while the enrichment (E) can then be calculated by equation 7.

$$R = n_{eq} \times 100 / C_i V_d = (K_{a/d} V_a \times 100)/(K_{a/d} V_a + V_d) \quad (6)$$

$$E = C_d / C_i = V_d R / V_a \times 100 \quad (7)$$

Equation 7 can be used to calculate the theoretical recoveries and enrichment for both LLE and LPME. For the three phase system (donor, supported liquid membrane, acceptor), the mass balance can be expressed by eq. 8:

$$n_i = n_d + n_{org} + n_a \quad (8)$$

where $n_{org}$ represents the mass of analyte in the supported liquid membrane. Equation 8 can also be expressed as $$C_i V_d = C_{eq[d]} V_d + C_{eq[org]} V_{org} + C_{eq[a]} V_a \quad (9)$$

where $C_{eq[org]}$ corresponds to the concentration of analyte in the supported liquid membrane at equilibrium and $V_{org}$ is the volume of the organic membrane phase.

In a three phase system, there will be two distribution constants which represent the two equilibria occurring in this system, as given in equations 10 and 11, respectively.

$$K_{org/d} = C_{eq[org]}/C_{eq[d]} \quad (10)$$

$$K_{a/org} = C_{eq[a]}/C_{eq[org]} \quad (11)$$

$K_{a/d}$ can be computed by equation 12:

$$K_{a/d} = K_{org/d} + K_{a/org} \quad (12)$$

from which we can derive equation 13:

$$K_{a/d} = (C_{eq[org]}/C_{eq[d]})(C_{eq[a]} C_{eq[org]}) = C_{eq[a]}/C_{eq[d]} \quad (13)$$

where $K_{org/d}$, $K_{a/org}$ and $K_{a/d}$ are the distribution constants between the pair of phases organic and donor, acceptor and organic and acceptor and donor, respectively.

The amount of analyte extracted into the acceptor phase of the system can be calculated by substituting $K_{a/d} C_{eq[d]}$ for $C_{eq[a]}$ in equation 9. Rearrangement leads to equation 14:

$$n_{eq} = (K_{a/d} V_a C_i V_d)/(K_{a/d} V_a + K_{org/d} V_{org} + V_d). \quad (14)$$

Then, the recovery R can be expressed as $$R = (n \times 100)/(C_i V_s) = (K_{a/d} V_a \times 100)/(K_{a/d} V_a + K_{org/d} V_{org} + V_d). \quad (15)$$

Finally, the enrichment E can be calculated using equation 16:

$$E = C_d / C_i = (V_d \times R)/(V_a \times 100). \quad (16)$$

ince the three phase system in LPME involves back extraction, this technique differs from LLE in that the extraction of the sample from the matrix into the organic phase and then from the organic phase into the acceptor phase occurs simultaneously in LPME, while it is a two step process in LLE. However, equations 15 and 16 can be used to predict recovery and enrichment in both processes approximately.

Preferred Device Formats/Geometries:

FIG. 1-A shows an isometric view of a multi-well plate 20 according to a presently preferred embodiment of the present invention. Plate 20 comprises a 96-well block 22, and a top plate 24 secured to block 22. Block 22 comprises an array of evenly-spaced sample wells each having a top opening. Top plate 24 comprises a plurality of analyte-collection through holes (apertures) 26, each corresponding to one of the wells of block 22.

FIG. 1-B shows a side sectional (1-1') view of an exemplary well 30 of block 22, and the corresponding part of top plate 24 extending over well 30. The top of through hole 26 includes a cone-shaped tapered surface 34, and functions as an inlet/outlet port. The tapered shape of surface 34 facilitates the entry of a transfer device such as a needle into hole 26. Top plate 24 comprises a projected tubular end 32 extending downward into well 30. Projecting end 32 can be integrally formed as one piece together with the planar part of top plate 24, or can be a separate part such as a resin tube attached to the planar part of top plate 24.

A hollow fiber 36 in a single-rod format is connected to projected end 32 along its top open side. The connection between the projected end 32 and the fiber 36 can be effected by well-known technologies, such as binding with an adhesive or by direct extrusion of fiber 36 through end 32. A bottom end 40 of fiber 36 is closed. Bottom end 40 is preferably formed by a sealant such as an adhesive or a plastic. To seal bottom end 40, an open-ended fiber may be placed on a heated plastic surface. Liquid plastic then enters the fiber through the open end, and cools to close the fiber end. An interior cavity 38 formed within hollow fiber 36 is separated from any liquid present in well 30 by the wall of fiber 30.

The projected end 32 with the connected fiber 36 fits into the corresponding well 30 of block 22. The entire top plate 24 and the well block 22 can be locked or secured to each other by a hook mechanism. The contact surface between top plate 24 and well block 22 is preferably tight fitting, so as to create a sealed environment. For ease of manufacturing and quality control each top through hole 26 is preferentially located coaxially with the center of the corresponding well 30. Well 30 can be designed to hold different volumes by varying its depth, such that different lengths of fiber 36 are accommodated within well 30.

A sample solution is dispensed into well 30 with an auto-dispenser or manually, as desired. An acceptor liquid or solution is then injected into cavity 38, on the lumen side of hollow fiber 36 with the injector system of a liquid chromatograph or any other robotic system. Prior to injection of the acceptor solution, fiber 36 is preferably precoated with the membrane-forming solution. After a specified period of time, the enriched and purified analyte solution can be sampled directly from cavity 38 through the same outlet 26, by the same auto-sampler or robotic system. A vibrator can be located underneath the well block 22 to assist in the efficient extraction of the analyte(s) of interest from the sample into the acceptor solution.

In an alternative embodiment depicted in FIG. 1-C, provision is made for an additional conically shaped sample inlet through-hole 46 defined through a top plate 24'. Through hole 46 extends over well 30 along an area external to fiber 36, such that hole 46 is not in direct communication with cavity 38. Hole 46 serves as an inlet for auto-dispensing of the sample solution to well 30 while plate 24' is mounted on well block 22. Hole 46 can also be useful when viscous samples, not injectable by autodispenser needles, or suspension-type samples are to be introduced into the well, as for example aqueous-oil mixtures. Such viscous samples can be inserted through hole 46 using a pipetter or other suitable device. Alternately, if a microscale organic synthetic reaction is carried out in the well, hole 46 can be used to introduce reagents into well 30. The reaction product can diffuse through membrane 36 into cavity 38, and can be analyzed directly. Such arrangements are especially useful in separating tritylated products from unreacted oligonucleotides.

As shown in FIG. 1-D, one or more strip-shaped partial top plate(s) 48 can be used instead of a global (x-y) top plate such as the top plate 24 shown in FIG. 1-A. Using partial top plate 48 can be convenient if, for example, only one segment of eight or twelve well plates, but not the entire cross section of ninety six wells, is needed for an extraction. Partial top plate 48 can carry twelve holes 26 evenly distributed in the same row with one single hollow fiber 36 connected to each of the holes 26 in this row. The fiber suspension arrangement for each hole 26 is similar to the one described with reference to FIG. 1-A and 1-B. A seal mat (not shown) can be used to cover the open well holes of block 22 not covered by top plate(s) 48.

FIG. 1-E shows a side sectional view of another geometry for a sample preparation plate 120 according to the present invention. Plate 120 comprises a 96-well block 122 fitted with a top flexible seal mat 124. Seal mat 124 can extend over the entire top surface of block 122. Seal mat 124 can also form an elongated strip extending over a single row of wells formed in block 122. Block 122 includes 96 evenly distributed wells 130, one of which is shown in FIG. 1-E. A seal stud 134 individually extends and tightly fits into each respective top opening 135 of a well 130. Seal stud 134 forms part of seal mat 124. An open end of a precoated single hollow fiber 36 is connected to a tube 137 which passes through seal stud 134.

A support material 141 such as a resin may be filled around tube 137 so as to position tube 137 rigidly within well 130. Support material 141 may be the same material used for the flat part of seal mat 124 and/or seal stud 134. The top end of tube 137 is connected to a funnel 139. Funnel 139 facilitates the access of a transfer device such as a needle to the interior cavity defined within fiber 36. Tube 137 and funnel 139 can be formed of a material such as a plastic or a metal such as stainless steel.

As illustrated in FIG. 1-F, an injection port 46' can be provided along the bottom of a well 30 defined in a multi-well block 23. To insert a sample into well 30, the plate is flipped over such that injection port 46' is positioned along the top surface of the plate. A sample is injected through port 46' manually or automatically, port 46' is sealed, and the plate is flipped back to the position illustrated in FIG. 1-F. The acceptor solution is then injected through hole 26, and after a desired period of time the analytes of interest are extracted through hole 26. The geometry of FIG. 1-F facilitates forming block 22 and upper plate 24 as a single monolithic piece.

As shown in FIG. 2-A, a tubular, tapered fiber-protecting insert 80 can be disposed laterally around fiber 36, in order to protect fiber 36 from contact with external structures during the assembly or operation of the sample preparation plate. Such contact can result in the crumpling, twisting, or collapse of fiber 36. Insert 80 can form part of upper plate 24. Insert 80 can be integrally formed as one piece together with the planar part of upper plate 24, or can be attached to the planar part of upper plate 24 using for example an adhesive, a fastener, or a press fit. Insert 80 hangs down from the lower flat surface of upper plate 24 into well 30, and is centered around fiber 36 and aperture 26. Insert 80 is longer than the longitudinal extent of fiber 36, such that insert 80 extends below fiber 36. The bottom end of insert 80 is open, so as to allow the liquid within well 30 to contact fiber 36. Insert 80 preferably has a downward-narrowing tapered shape. The tapered shape facilitates the entry of insert 80 into well 30. Insert 80 preferably has an annular upper contact section 82 situated along the flat surface of upper plate 24. Contact section 82 is sized to fit snugly within well 30, such that a press fit is established between insert 80 and well block 22 along the surface of contact section 82 when block 22 and upper plate 24 are fully engaged together.

In addition to insert 80, a global protective sidewall can be provided along the external boundary of upper plate 24, in order to provide global mechanical protection to all fibers 36. Insert 80 can also include round perforations extending through the surface of insert 80, so as to allow the fluid flow across insert 80. The perforation size/diameter can be on the order of millimeters or less, such that fluid can flow unimpeded through insert 80, while fiber 36 remains mechanically protected from outside contact. As illustrated in FIG. 2-B, insert 80 can be provided as part of an intermediate plate 90 stacked between a top plate 24' and well block 22. Intermediate plate 90 can also be thought of as forming part of the top plate.

As illustrated in FIG. 3, one or more elongated alignment/protection pins 92*a-b* can be provided as part of an upper plate 24", for each well 30 of a well block 22". Pins 92*a-b* preferably extend along at least the entire length of fiber 36, and are disposed around fiber 36. Pins 92*a-b* ensure the alignment of each fiber 36 within its corresponding well 30, and laterally protect fiber 36 from contact with external structures. Each pin 92*a-b* fully fits through a corresponding longitudinal guiding hole 94*a-b* defined within block 22". Guiding holes 94*a-b* are located between adjacent wells 30. An annular seal flange 96 can be provided along the top of fiber 36, for sealing well 30 when upper plate 24" is fully engaged to well block 22". Seal flange 96 forms part of upper plate 24". Seal flange 96 is attached to the bottom surface of the planar part of upper plate 24", and is centered around fiber 36. The external lateral surface of seal flange 96 is sized to fit snugly within well 30.

FIG. 4-A shows an isometric view of a multi-well plate 220 according to an alternative embodiment of the present invention. Plate 220 comprises a receiving base plate 222 having an array of holes defined therethrough, and a plurality of tubes (cartridges) 252 mounted on base plate 222. Each tube 252 is mounted through one of holes defined in base plate 222. Preferably, the cross section of each tube 252 is circular or square-shaped.

FIG. 4-B shows a side sectional view through an exemplary tube 252 and a part of base plate 222 below the shown cartridge 252. Base plate 222 may include a plurality of individual wells each corresponding to each tube 252, or a global cavity situated underneath the holes of plate 222, common to all tubes 252. Each tube 252 can be connected to base plate 222 pressing or screwing type of fit or any other connection mechanism. A bottom base block 258 may be used to support base plate 222, and to provide a desired height to plate 220, such that plate 220 optimally fits into an auto-sampler assembly of a liquid chromatographic system.

Each tube 252 includes a tube body 254 for holding a sample of interest, and a cap 256 mounted on top of tube body 254. An internal collection cavity 38 is defined within a hollow fiber 36, as described above with reference to FIGS. 1-A and 1-B. Hollow fiber 36 preferably hangs from a downward-protruding tubular stud structure 232 of cap 256. Cap 256 includes a top central opening 226 for providing access to cavity 38. Top cap 256 can be replaced with a partial plate (not shown) with multi-holes having appropriately connected fibers in the bottom. The partial plate can be inserted to cover a segment defined by multiple tubes 252. A seal strip and seal cap can be applied to any open tubes 252 not covered by this partial plate The bottom end of fiber 36 can be closed, as shown in FIG. 4-B. The bottom end of fiber 36 can also be mounted on a second stud (not shown) positioned underneath stud 232, such that fiber 36 is held between the two studs. Fiber 36 then has two open ends: an upper inlet and a lower outlet. In such an arrangement, the acceptor solution containing the analyte(s) of interest can be collected through a bottom aperture of the tube, into a corresponding well positioned underneath the bottom opening. The bottom aperture of the tube is connected to the second (lower stud). The bottom aperture is held closed while the analyte of interest collects inside the fiber volume, and is opened after a period of time in order to allow the acceptor solution to flow out.

As in the monolithic multi-well plate described with reference to FIGS. 1-A and 1-B, a sample solution is disposed in each tube 252 with an auto-dispenser device. An acceptor solution is injected through the inlet/outlet hole 226 into the cavity 38 defined within hollow fiber 36, using an auto-sampler injector or robotic system. The acceptor solution containing the extracted sample in cavity 38 can be drawn off through the same inlet/outlet hole 226 by the auto-sampler or robotic system.

Figure 5:
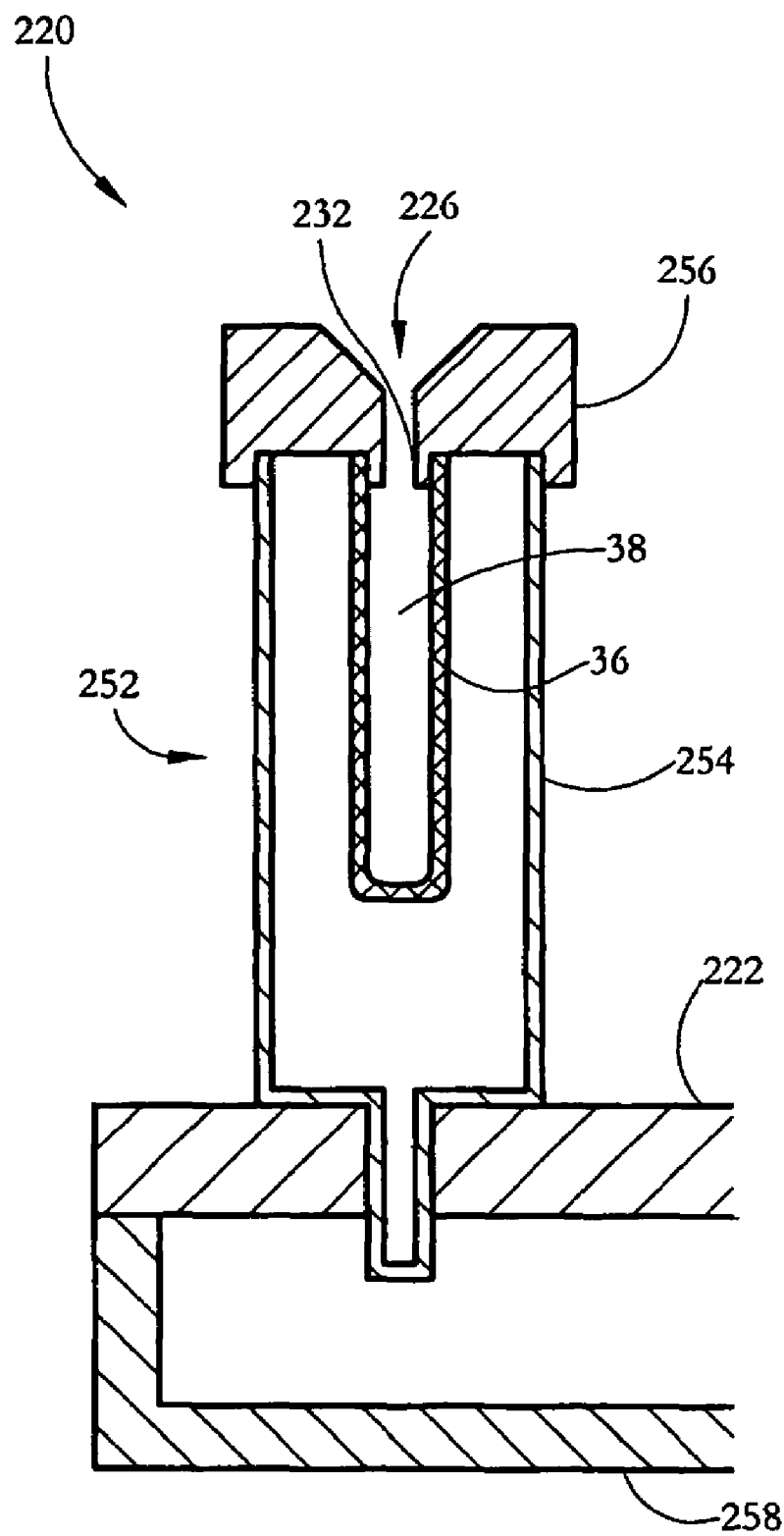
FIGS. 5-A through 5-C illustrate three different hollow fiber geometries according to other embodiments of the present invention.

FIG. 5-A illustrates part of a sample preparation plate 320 according to another embodiment of the present invention. Plate 320 includes a multi-well block 322, and a top plate 324 mounted on and covering block 322. An inlet adaptor 343 is built on the top plate 324, above a well 330. Inlet adaptor 343 has an open top inlet 349, and two bottom outlets 344, 345 arranged orthogonal to each other. A single U-shaped hollow fiber 336 has two open ends 347, 348 respectively connected to outlets 345, 344.

The illustrated hollow fiber geometry facilitates a reduction in the formation of air bubbles inside hollow fiber 336. As acceptor liquid is inserted vertically into well 330 through the fiber segment aligned with inlet 349, the air initially present within fiber 336 can escape upward through the other segment of fiber 336, away from the incoming liquid. The shown geometry also facilitates uniform distribution of the acceptor liquid within hollow fiber 336. The illustrated U-shaped hollow fiber geometry also allows the use of a hollow fiber 336 longer than the depth of the corresponding well 330.

FIG. 5-B illustrates part of a sample preparation plate 420 according to another embodiment of the present invention. Plate 420 includes a multi-well block 422, and a top plate 424 mounted on block 422. An H-shaped adaptor 443 is formed through top plate 424, above a well 430. Adaptor 443 includes two inlet ports 449, 449' and two corresponding outlet ports 445, 445'. Outlet ports 445, 445' are respectively connected to two rod-shaped hollow fibers 436, 436'. The illustrated hollow fiber geometry facilitates different kinds of possible extraction combinations such as forward and back extractions. The horizontal tube of adaptor 443 serves as an air vent.

FIG. 5-C illustrates part of a sample preparation plate 520 according to another embodiment of the present invention. Plate 520 includes a multi-well block 522, and a top plate 524 mounted on block 524. Two parallel tubes 557, 558 project vertically through top plate 524, above a well 530. A U-shaped hollow fiber 536 has two open ends 555, 556 connected to tubes 557, 558, respectively. The top ends of the tubes 557, 558 to a small funnel 559 and an open cap 560, respectively, which are positioned on the topside of the plate 524. The funnel 559 can serve as an inlet and/or outlet port. The open cap 560 can function as an outlet, a pressure equalizer, or a vent for any air inside hollow fiber 536. As described above, tubes 557, 558 can be formed from a plastic or a metal such as stainless steel, among others.

FIG. 6 is a schematic illustration of part of a sample preparation plate 620 according to another embodiment of the present invention. Plate 620 comprises individual vials 652 mounted in corresponding wells 630 defined in a base plate 622. Each well 630 can carry vials of different sizes and or volumes—for example, 4 mL or 2 mL volumes. Each vial 652 comprises a tubular vial container 654 defining a well 630 for holding a sample of interest, a vial cap 656 mounted on vial container 654, and a hollow fiber sample preparation structure 636 hanging from vial cap 656 into well 630. Vial cap 656 can be press fitted, screw fitter, or otherwise fastened by known means to vial container 654. Vial cap 656 and the attached hollow fiber structure 636 can have any of the geometries illustrated in FIGS. 1-B through 5-C. In the arrangement shown in FIG. 6, the collection of individual vials 652 effectively forms a modular sample preparation multi-well plate, while the collection of vial caps 656 of vials 652 effectively forms a modular fiber membrane support supporting a plurality of hollow fiber membranes disposed in the wells of the multi-well plate.

FIG. 7 shows part of a multi-well plate 720 according to another embodiment of the present invention. Plate 720 comprises a multi-well block 722 defining a plurality of collection wells 729, and a multi-aperture top plate 724 mounted on block 722. A pre-coated disk-shaped porous membrane support 771 is mounted in a deep counterhole 774 defined within top plate 724. Membrane support disk 771 rests on an annular protrusion that prevents disk 771 from sliding downward. A sample-holding well 730 is defined in the area enclosed by top plate 724 and situated above disk 771. To perform LPME in the well shown in FIG. 7, the sample of interest is preferably placed in sample-holding well 730, while the acceptor solvent is placed in collection well 729 so as to contact disk 771. After the analytes of interest have passed from sample holding well 730 into collection well 729 through the liquid membrane defined in the pores of disk 771, top plate 724 is removed and the enriched and purified analytes of interest are collected from collection well 729.

FIGS. 8-A and 8-B shows side sectional and top views, respectively, of part of a sample preparation plate 820 according to another embodiment of the present invention. An annular support structure 824 is mounted in a centered position above a sample-holding well of a multi-well block (not shown). Support structure 824 can be a vial cap as illustrated in FIGS. 6 and 4-A-B, or form part of a partial or whole top cover plate as illustrated in FIGS. 1-A through 5-C.

A concave, U-shaped or V-shaped collection microcontainer 876 is disposed below a collection aperture 826 defined in support structure 824. Microcontainer 876 can preferably hold up to 100 microliters of a fluid. One end of a U-shaped hollow fiber 836 is connected to an inlet tube which passes through an opening 877 provided in support structure 824 into the sample-holding well. The other end of hollow fiber 836 is connected to an inlet of a collection tube 878. An outlet of collection tube 878 is disposed in/above collection microcontainer 876. Hollow fiber 836 is held by its end connections to the inlet and collection tubes, and hangs into the sample-holding well so as to contact a sample of interest held in the sample-holding well.

Acceptor fluid is inserted into hollow fiber 836 through inlet tube 877. After the analytes of interest have passed from the sample-holding well into the acceptor fluid held in hollow fiber 836, positive pressure is applied through inlet tube 877 so as to evacuate the contents of hollow fiber 836 through collection tube 878 into collection microcontainer 876. The enriched and purified analytes of interest can then be removed from collection microcontainer 876 using an autosampler needle of a chromatographic instrument or other known devices.

The plate geometry illustrated in FIGS. 8-A and 8-B reduces the chance that an autosampler needle used for collecting the acceptor solution damages hollow fiber 836. The illustrated geometry allows increased flexibility in the choice of hollow fiber membrane shapes and internal diameters, and in the diameter of the needle used to collect the analytes of interest.

The single vials described above can be used individually or mounted on a sampler plate on a LC instrument. Such single vials can be produced by fitting commercially available or custom made products with the described hollow fiber membranes and associated support structures. Alternative formats and/or modifications can be visualized by those skilled in the art relating to the above detailed descriptions. Such modifications should be deemed to be within the same scope of the present invention.

Separation and Enrichment of Pharmaceuticals:

The description below focuses on the application of the multiple sampling devices described above to the extraction of trace levels of pharmaceuticals and other small molecules in aqueous media or biological matrices using 10 to 50 microliter volumes of acceptor (or strip) phase, preferably 25 microliters, to obtain optimal enrichment. Such enrichment is useful in producing measurable signals by the analytical instruments utilized for the analysis of pharmaceuticals at the nanogram or picogram level, especially when dealing with mixtures of analytes. Such analytical instruments can include high performance liquid chromatographs, gas chromatographs, capillary electrophoretic instruments, mass spectrometric detectors, and others. Sample volumes of 500 μL or even less from the lower end up to 25 mL on the higher end can be utilized for extraction and enrichment with the well plate or vial forms of devices disclosed in the current invention. When the analytes under investigation are basic drugs, the sample solutions are treated with a base such as sodium hydroxide or ammonia to bring the pH of the matrix to around 7.0 or over. These basic analytes will then exist as free bases and not in the form of salts, to facilitate extraction across the membrane barrier. Conversely, if the matrix contains acidic pharmaceuticals, its pH is adjusted to be around 2.0 to 5.0 so that the acids exist in the free state and do not form carboxylate anion structures. For the extraction and enrichment of basic analytes, acidic acceptor solutions are used, as for example, 0.1M hydrochloric acid or acetic acid. For acidic analytes, 0.1M sodium hydroxide or sodium carbonate could be utilized.

The supported liquid membrane layer could be predeposited on to the hollow fiber prior to fitting of the fiber into the device, for coatings that can form stable membranes. Polymeric membranes are quite stable over long periods of time and have excellent diffusion characteristics for a wide range of analytes. By the same token, monomeric materials can be initially introduced into the pores of the hollow fiber and then polymerized in situ. For coatings that do not form stable membranes over extended periods of time, the fiber can be dipped into a solution of the coating material. The device formats described above facilitate the coating of fibers with the membrane forming liquids or solids by simple dipping of the cover plates carrying the fibers into the membrane forming solutions, as these cover plates are easily detachable from the well plates. After coating, the cover plates can be put back on to the well blocks, after washing off excess coating material sticking to the fiber. If the membrane forming material is a solid, a solution of the membrane forming solid in an appropriate solvent can be introduced into a container such as a vial or well plate either manually or through an automatic dispenser. A membrane forming liquid material can be used as such for coating the fiber. A supported liquid membrane can be polar or hydrophobic in nature, depending upon the chemical nature of the analyte being extracted. Polyethers, polyesters, polyurethanes, polyamides, polyvinylalcohol, polyalkylene glycols and polyacrylonitrile derivatives can be used to form polar coatings, to mention a few examples. Hydrophobic coatings include, but are not restricted to, hexadecane, polyalkylenes, polyalkenes with phenylenyl moieties. Each one of the fibers in the 48 or 96 or 384 well plate device format can be coated with a different membrane material, if needed.

Acceptor Phase Selectivity:

When extraction of basic pharmaceuticals from aqueous solutions or human fluids is carried out, the sample solutions are rendered basic to keep the drugs in the free state. A variety of acidic acceptor solutions are available for extraction of these basic drugs, such as the mineral acids (hydrochloric, nitric, sulfuric), organic acids (formic, acetic, propionic acids) or acidic buffers (such as phosphate or acetate or citrate buffers whose pH has been adjusted to be in the range 2.0 to 5.0). However, one is not restricted to these alone, and can use a wider selection of acidic materials. Strong acids may not be suitable for use with silica-based solid phase extraction sorbents, since the bonded phases can be cleaved off under such conditions. The current membrane based devices have this clear advantage over the silica-based SPE bonded phases. Tables 1-A through 1-C show extraction recovery data for seven basic drugs making use of 16 acidic acceptor solutions. Tables 1-A and 1-B show extraction recovery values and enrichment values, respectively. Table 1-C shows extraction recovery values averaged over the seven drugs.

TABLE 1-A

Extraction recovery with different acceptor phases

| Acceptor phase | Measured pH | Extraction recovery (average of 3 replicates) | | | | | | |
|---|---|---|---|---|---|---|---|---|
| | | #1 | #2 | #3 | #4 | #5 | #6 | #7 |
| 10 mM HCl | 2.1 | 51% | 76% | 80% | 79% | 86% | 83% | 43% |
| 100 mM HCl | 1.2 | 46% | 75% | 87% | 86% | 84% | 88% | 53% |
| 10 mM H$_2$SO$_4$ | 2.1 | 65% | 88% | 90% | 76% | 98% | 87% | 35% |
| 100 mM H$_2$SO$_4$ | 1.3 | 61% | 84% | 88% | 85% | 94% | 99% | nd |
| 10 mM HNO$_3$ | 1.9 | 30% | 78% | 66% | 75% | 88% | 85% | 49% |
| 100 mM HNO$_3$ | 1.1 | nd | nd | 40% | 85% | 67% | 61% | 39% |
| 10 mM H$_3$PO$_4$ | 2.5 | 45% | 60% | 61% | 74% | 60% | 61% | 30% |
| 100 mM H$_3$PO$_4$ | 1.8 | 36% | 52% | 56% | 50% | 48% | 56% | 29% |
| 10 mM HCOOH | 3.1 | 45% | 66% | 72% | 45% | 71% | 70% | 8% |
| 100 mM HCOOH | 2.3 | 3% | 8% | 66% | 58% | 57% | 62% | 31% |
| 10 mM CH$_3$COOH | 3.3 | 41% | 58% | 60% | 20% | 54% | 54% | 5% |
| 100 mM CH$_3$COOH | 2.7 | 30% | 48% | 56% | 41% | 53% | 53% | 12% |
| 10 mM phosphate | 3.3 | 77% | 85% | 87% | 52% | 84% | 84% | 12% |
| 100 mM phosphate | 3.0 | 80% | 83% | 82% | 58% | 73% | 80% | 32% |
| 10 mM acetate | 4.8 | 56% | 80% | 57% | 2% | 26% | 24% | nd |
| 100 mM acetate | 4.8 | is | is | 66% | is | 26% | 25% | nd |

1 = amphetamine,
2 = methamphetamine,
3 = pethidine,
4 = chlorcyclizine,
5 = methadone,
6 = haloperidol,
and #7 = buprenorphine;
nd = not detectable,
is = insufficient separation for accurate quantitation

TABLE 1-B

Enrichment with different acceptor phases

| Acceptor phase | Measured pH | Enrichment (average of 3 replicates) | | | | | | |
|---|---|---|---|---|---|---|---|---|
| | | #1 | #2 | #3 | #4 | #5 | #6 | #7 |
| 10 mM HCl | 2.1 | 82 | 122 | 128 | 126 | 138 | 133 | 69 |
| 100 mM HCl | 1.2 | 74 | 120 | 139 | 138 | 134 | 141 | 84 |
| 10 mM H$_2$SO$_4$ | 2.1 | 104 | 141 | 144 | 122 | 157 | 139 | 56 |
| 100 mM H$_2$SO$_4$ | 1.3 | 98 | 134 | 141 | 136 | 150 | 158 | nd |
| 10 mM HNO$_3$ | 1.9 | 48 | 125 | 106 | 120 | 141 | 136 | 78 |
| 100 mM HNO$_3$ | 1.1 | nd | nd | 64 | 136 | 107 | 98 | 62 |
| 10 mM H$_3$PO$_4$ | 2.5 | 72 | 96 | 98 | 118 | 96 | 98 | 48 |
| 100 mM H$_3$PO$_4$ | 1.8 | 58 | 83 | 90 | 80 | 77 | 90 | 46 |
| 10 mM HCOOH | 3.1 | 72 | 106 | 115 | 72 | 114 | 112 | 13 |
| 100 mM HCOOH | 2.3 | 5 | 13 | 106 | 93 | 91 | 99 | 50 |
| 10 mM CH$_3$COOH | 3.3 | 66 | 93 | 96 | 32 | 86 | 86 | 8 |
| 100 mM CH$_3$COOH | 2.7 | 48 | 77 | 90 | 66 | 84 | 84 | 19 |
| 10 mM phosphate | 3.3 | 123 | 136 | 139 | 83 | 134 | 134 | 19 |
| 100 mM phosphate | 3.0 | 128 | 133 | 131 | 93 | 117 | 128 | 51 |
| 10 mM acetate | 4.8 | 90 | 128 | 91 | 3 | 42 | 38 | nd |
| 100 mM acetate | 4.8 | is | is | 106 | is | 42 | 40 | nd |

1 = amphetamine,
2 = methamphetamine,
3 = pethidine,
4 = chlorcyclizine,
5 = methadone,
6 = haloperidol,
and #7 = buprenorphine;
nd = not detectable,
is = insufficient separation for accurate quantitation

TABLE 1-C

Average recovery for 7 drugs with different acceptor phases

| Acceptor phase | Average extraction recovery | Acceptor phase | Average extraction recovery |
|---|---|---|---|
| 10 mM HCl | 71% | 10 mM HCOOH | 54% |
| 100 mM HCl | 74% | 100 mM HCOOH | 41% |
| 10 mM H$_2$SO$_4$ | 77% | 10 mM CH$_3$COOH | 42% |
| 100 mM H$_2$SO$_4$ | 73% | 100 mM CH$_3$COOH | 42% |
| 10 mM HNO$_3$ | 67% | 10 mM phosphate | 69% |
| 100 mM HNO$_3$ | 42% | 100 mM phosphate | 70% |
| 10 mM H$_3$PO$_4$ | 56% | 10 mM acetate | 35% |
| 100 mM H$_3$PO$_4$ | 47% | 100 mM acetate | 39% |

The data in Tables 1-A through 1-C was generated by performing LPME using three different hollow fibers. The extractions were performed from water samples containing each component at the 100 ng/mL level.

Figure 9:
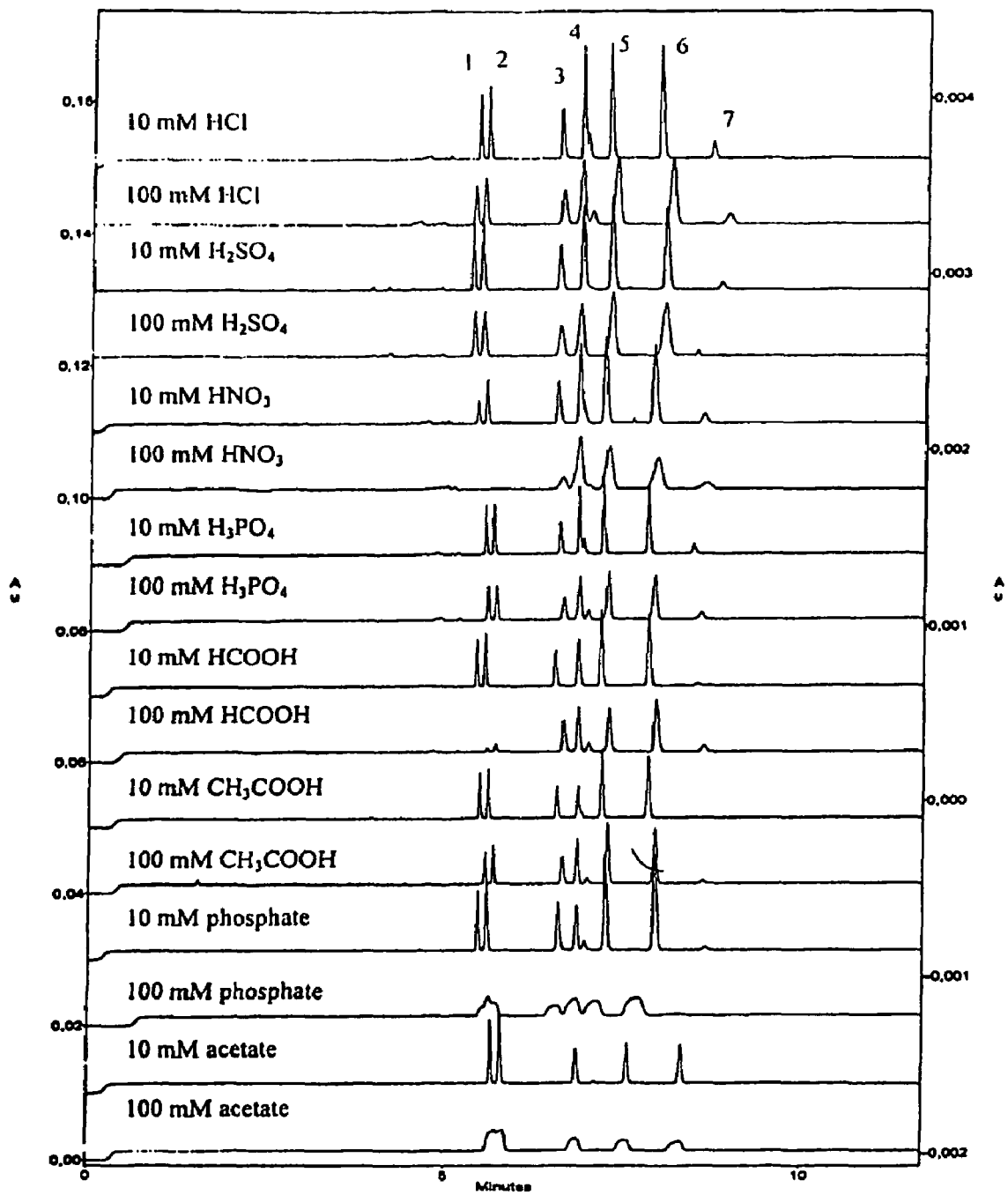
FIG. 9 shows capillary electropherograms of a seven component basic drug mix after LPME demonstrating acceptor phase selectivity.

Significant differences could be detected between the acids studied as acceptors. In general, mineral acids and phosphate buffers of low pH furnished the highest recoveries for the drugs. Lower recoveries were obtained with acetic and formic acids and acetate buffers and the discrepancies could be attributed to variation in acceptor phase pH, buffer capacity or the solubility of drugs with different counter ions. It is evident that a selective enrichment between basic drugs could be achieved by controlling the acceptor phase chemistry. The electropherograms of the seven drugs with different acidic acceptors are included in FIG. 9. The peaks labeled 1-7 in FIG. 9 correspond to the drugs labeled 1-7 in Table 1-A.

Figure 10:
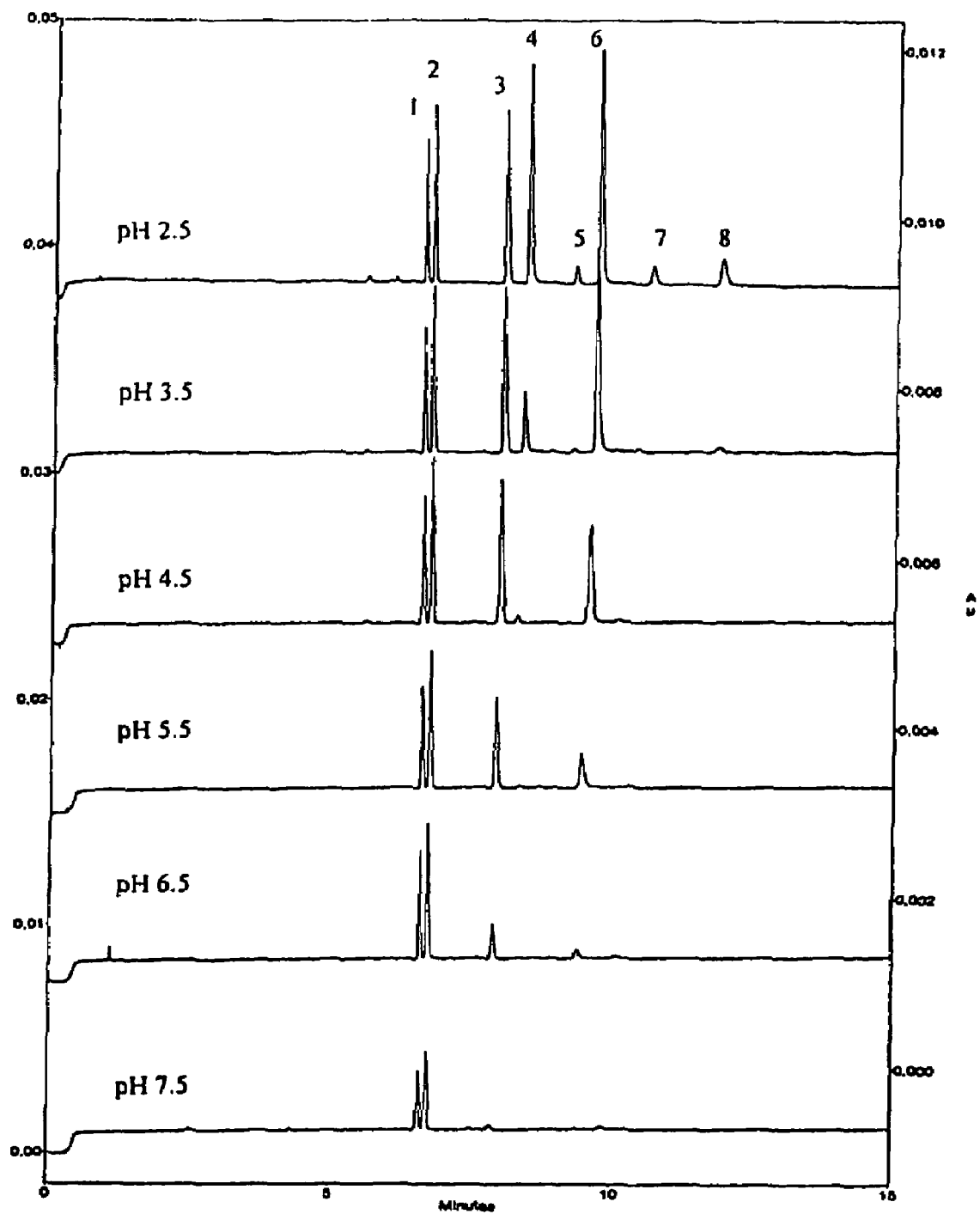
FIG. 10 shows capillary electropherograms of an eight component basic drug mix after LPME to demonstrate acceptor pH selectivity.

Selectivity from Acceptor Phase pH:

It is possible to vary the pH of the acceptor phase, during the extraction of basic drugs, by changing the pH of the buffer. FIG. 10 shows the electropherograms of eight basic drugs obtained by analyzing the extracts obtained by using phosphate buffers ranging from pH 2.5 to 7.5 as acceptor phases. Tables 2-A and 2-B show the selectivity obtained with basic drugs when acceptors of different pHs are used. The peaks labeled 1-8 in FIG. 10 correspond to the drugs labeled 1-8 in Tables 2-A-B.

TABLE 2-A

Extraction recovery with different acceptor phases

| | Extraction recovery (average of 3 replicates) | | | | | | | |
|---|---|---|---|---|---|---|---|---|
| pH | #1 | #2 | #3 | #4 | #5 | #6 | #7 | #8 |
| 2.5 | 67% | 94% | 100% | 77% | 5% | 105% | 2% | 11% |
| 3.5 | 64% | 91% | 92% | 20% | 1% | 83% | 1% | 1% |
| 4.5 | 65% | 94% | 82% | 3% | nd | 49% | nd | nd |
| 5.5 | 58% | 84% | 56% | nd | nd | 22% | nd | nd |
| 6.5 | 55% | 76% | 21% | nd | nd | 4% | nd | nd |
| 7.5 | 40% | 55% | 4% | nd | nd | nd | nd | nd |

1 = amphetamine,
2 = methamphetamine,
3 = pethidine,
4 = chlorcyclizine,
5 = noscapin,
6 = haloperidol,
7 = diazepam, and
8 = reserpin;
nd = not detectable

TABLE 2-B

Enrichment with different acceptor phases

| | Enrichment (average of 3 replicates) | | | | | | | |
|---|---|---|---|---|---|---|---|---|
| PH | #1 | #2 | #3 | #4 | #5 | #6 | #7 | #8 |
| 2.5 | 107 | 150 | 160 | 123 | 8 | 168 | 3 | 18 |
| 3.5 | 102 | 146 | 147 | 32 | 2 | 133 | 2 | 2 |
| 4.5 | 104 | 150 | 131 | 5 | nd | 78 | nd | nd |
| 5.5 | 93 | 134 | 90 | nd | nd | 35 | nd | nd |
| 6.5 | 88 | 122 | 34 | nd | nd | 6 | nd | nd |
| 7.5 | 64 | 88 | 6 | nd | nd | nd | nd | nd |

1 = amphetamine,
2 = methamphetamine,
3 = pethidine,
4 = chlorcyclizine,
5 = noscapin,
6 = haloperidol,
7 = diazepam, and
8 = reserpin;
nd = not detectable The extraction recovery and enrichment data demonstrates that at pH values below 3.0, all the basic drugs are extracted substantially completely. However, as pH increases progressively, there is a significant change in extractability of these basic drugs, especially beyond pH 6.0 and this is attributable to differences in the pK$_a$ values of the drugs investigated. These experiments clearly show that a mixture of basic drugs can be selectively extracted from aqueous matrices by controlling the pH of the acceptor phase.

Figure 11:
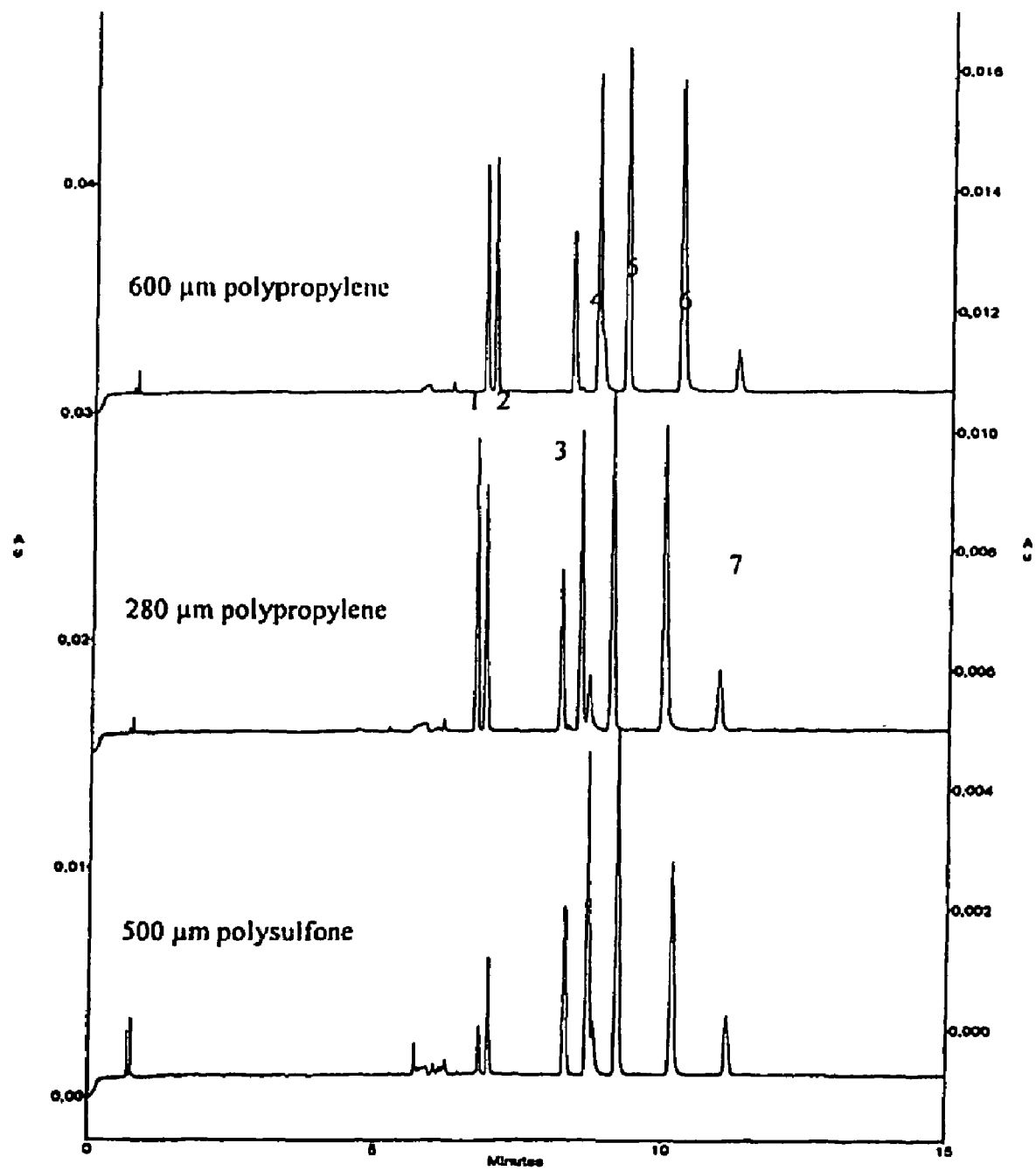
FIG. 11 shows capillary electropherograms of a seven component basic drug mix after LPME to demonstrate fiber selectivity.

Selectivity Based on Hollow Fiber Chemistry:

The differences in the hydrophobicity and polarity of the materials from which the hollow fibers are generated could be utilized for imparting selectivity to the fiber during the extraction process. We investigated polypropylene and polysulfone fibers for their capacities for extracting a mixture of seven basic drugs under identical conditions. The resulting data is presented in Tables 3-A and 3-B. Table 3-A lists measured extraction recovery values, while Table 3-B lists measured enrichment values. Capillary electrophoresis data is shown in FIG. 11. The peaks labeled 1-7 in FIG. 11 correspond to the drugs labeled 1-7 in Tables 3-A-B.

TABLE 3-A

Extraction recovery with different hollow fibres

| | Extraction recovery (average of 3 replicates) | | | | | | |
|---|---|---|---|---|---|---|---|
| Hollow fibre | #1 | #2 | #3 | #4 | #5 | #6 | #7 |
| Polypropylene, 600 μm ID | 51% | 76% | 80% | 79% | 86% | 83% | 43% |
| Polypropylene, 280 μm ID | 65% | 77% | 76% | 66% | 86% | 82% | 61% |
| Polysulfone, 500 μm ID | 14% | 35% | 78% | 69% | 87% | 54% | 58% |

1 = amphetamine,
2 = methamphetamine,
3 = pethidine,
4 = chlorcyclizine,
5 = methadone,
6 = haloperidol, and
7 = buprenorphine

TABLE 3-B

Enrichment with different hollow fibres

| Hollow fibre | Enrichment(average of 3 replicates) | | | | | | |
|---|---|---|---|---|---|---|---|
| | #1 | #2 | #3 | #4 | #5 | #6 | #7 |
| Polypropylene, 600 μm ID | 82 | 122 | 128 | 126 | 138 | 133 | 69 |
| Polypropylene, 280 μm ID | 104 | 123 | 122 | 106 | 138 | 131 | 98 |
| Polysulfone, 500 μm ID | 22 | 46 | 125 | 110 | 139 | 86 | 93 |

1 = amphetamine,
2 = methamphetamine,
3 = pethidine,
4 = chlorcyclizine,
5 = methadone,
6 = haloperidol, and
7 = buprenorphine A significant selectivity difference could be noticed in the case of amphetamine and methamphetamine, with polysulfone exhibiting much lower recoveries. Further, a similar effect was also evidenced with haloperidol, although to a much smaller extent.

Figure 12:
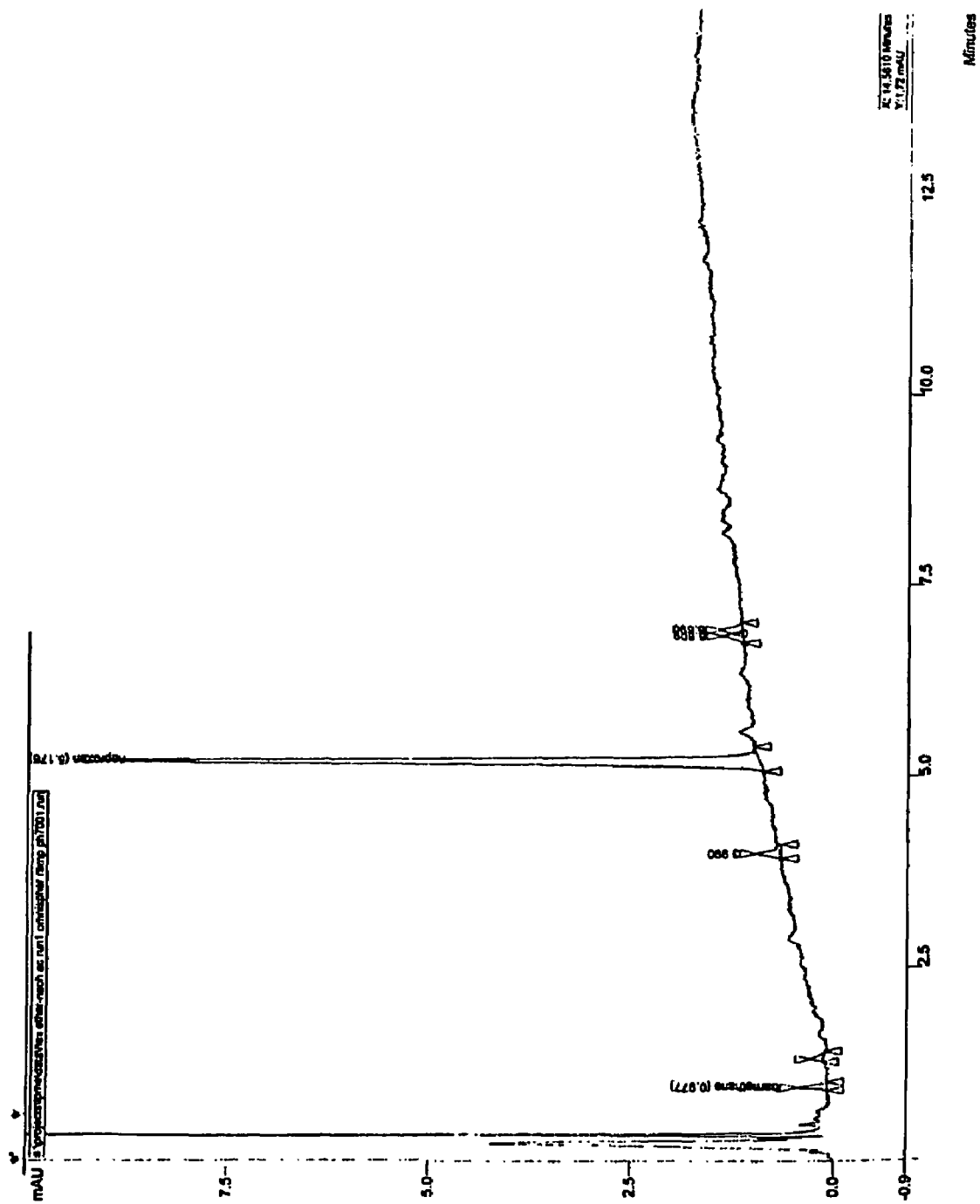
FIGS. 12-A-B show chromatograms from the HPLC of a five component acid/base drug mixture after LPME with four different membrane forming liquids to demonstrate membrane selectivity and selective extraction of acidic and basic drugs with basic and acidic acceptors, respectively.

Selectivity Based on Membrane Chemistry:

Little information was previously available on the differences in the behavior of membranes in the separation process. We have used the multiple sampling device to demonstrate the selectivity of four different membrane liquids, i.e. hexyl ether, 2-octyl-1-dodecanol, 1-octanol and 4-nitrophenyl octyl ether. A fifth material, N-octyl 2-pyrrolidone, did not show good extraction capability for the tested application. A mixture of acidic and basic drugs was used in this study, together with 0.1 M hydrochloric acid or 0.1 M sodium hydroxide as the acceptor phase. The chromatograms presented in FIGS. 12-A-B along with the data in Table 4 indicate that the four membranes have different selectivity to the basic probes. FIG. 12-A shows a chromatograph illustrating the enrichment of naproxen using a nitrophenyl octylether membrane and a 0.1 M sodium hydroxide acceptor. FIG. 12-B shows a chromatograph illustrating the enrichment of doxepin and quinidine with a nitrophenyl octylether membrane and a 0.1 M hydrochloric acid acceptor. The basic drugs are preferentially extracted into the hydrochloric acid acceptor from a basified sample solution, while the acidic drugs are selectively extracted into the sodium hydroxide acceptor from an acidified sample solution.

TABLE 4

Enrichment of Quinine and Doxepin on Different Liquid Membranes

| Supported Liquid Membrane Material | Enrichment of Quindine | Enrichment of Doxepin |
|---|---|---|
| Hexyl Ether | 100 | 202 |
| 4-nitrophenyl octyl ether | 52 | 227 |
| 1-octanol | 100 | 58 |
| 2-octyl-1-dodecanol | 20 | 147 |

Operation of the Devices and Sample to Acceptor Volume Ratios:

The devices described above operate in a static mode, as opposed to a mode in which the acceptor solution circulates through the membrane fibers. In a static mode, the sample and/or acceptor solution may be vibrated inside their container(s), but do not flow through the fiber. The extractions are typically completed within 15 to 30 minutes, depending upon the nature of the sample. With whole blood or plasma samples, about 30 minutes may be used to complete the extraction step. With simpler aqueous sample solutions, extraction times as low as 5 minutes can be sufficient to attain equilibrium between the sample solution and the acceptor phase.

The donor sample preferably has a volume higher than 200 μL and lower than 25 ml. Sample volumes on the order of 500 μL can be readily employed. The acceptor solution preferably has a volume higher than 10 μL and lower than 500 μL. Acceptor solution volumes volumes lower than 100 μL can be readily employed, and acceptor volumes between 20 and 50 μL are commonly utilized. If the fiber dimensions are as small as 4 to 5 cm, 10 μL of acceptor can be sufficient. Longer fibers can hold larger amounts of acceptor solution. The current device facilitates the use of fibers of any desired dimension. The length of the employed fiber is preferably between 1 cm and 20 cm, and is commonly longer than 2 cm. In common implementations, the inner diameter of the fiber is between 0.3 mm and 1.5 mm, and preferably between 0.6 mm and 1.2 mm. The hollow fiber has an average pore size in a range between 0.02 μm and 2 μm. A present implementation employs fibers with lengths of 7 to 8 cm, 500 micron inner diameter, 0.2 micron pore size, and an acceptor phase volume of 25 μL.

The ratio between the sample solution to acceptor solution volume can vary typically from 20 to 200, while equilibration times can still be in the 15 to 30 minute range. Adjustment of the acceptor solution volume can be used to control the sample enrichment. This ratio can be controlled by employing fibers of appropriate length or thicker fibers can be made use of if larger acceptor volumes are needed to be used.

If a collection needle comes into close proximity with a hollow fiber, it is preferred that the needle diameter be less than half the size of the internal diameter of the hollow fiber, such that the collection needle does not damage or puncture the fiber. Increasing the diameter of a hollow fiber may require increasing its wall thickness, in order to preserve the mechanical stability of the fiber. At the same time, increasing the fiber wall thickness can lead to unacceptably long time periods required to achieve desired levels of enrichment. For typical fiber compositions, it was observed that fiber diameters larger than about 1.2 mm may require fiber walls thicker than about 200 μm for mechanical stability. At the same time, increasing the fiber wall thickness to over about 200 μm was observed to lead to a marked increase in the time required to achieve useful levels of enrichment.

EXAMPLES

Figure 13:
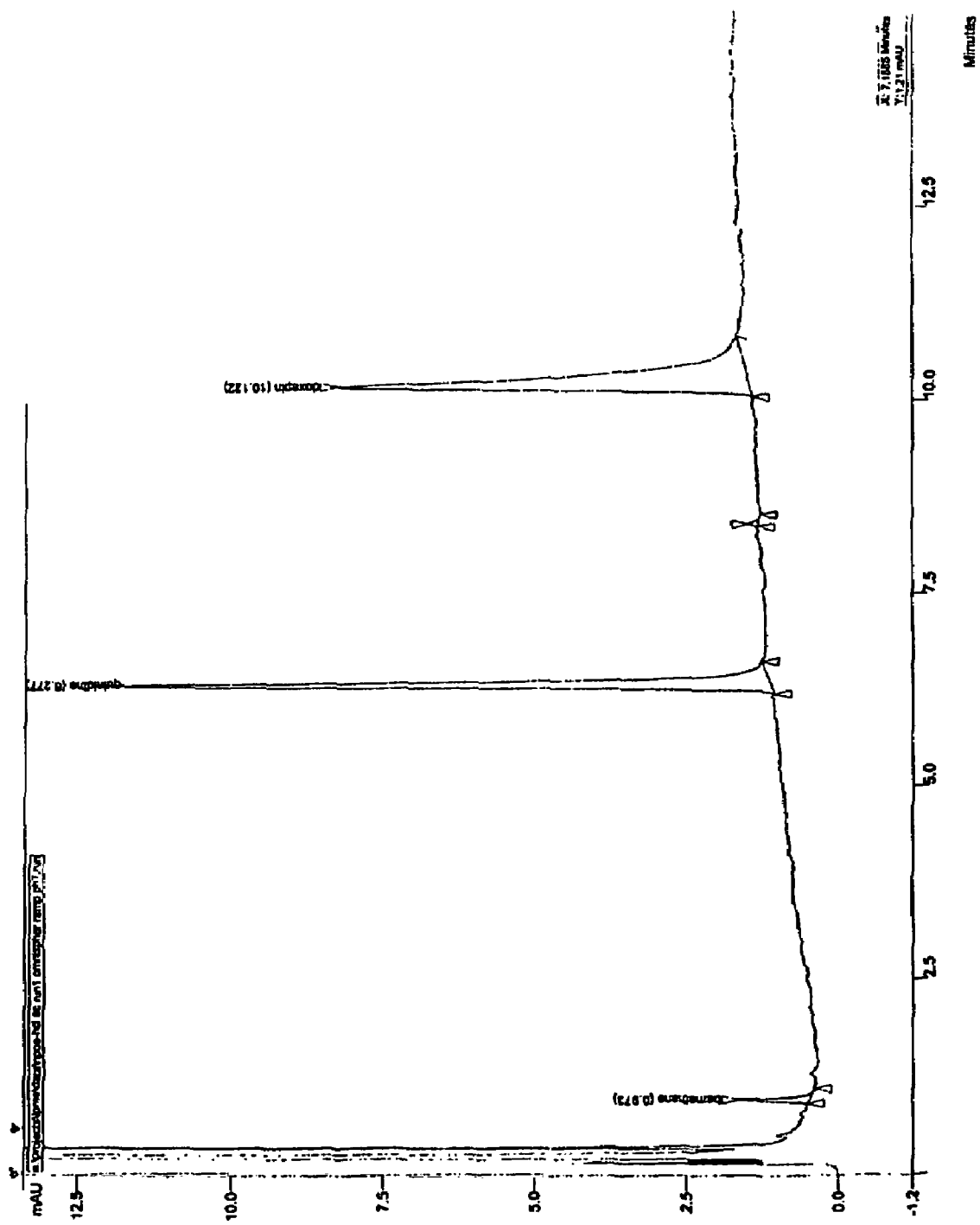
FIGS. 13-A-B show electropherograms of methamphetamine from human urine and plasma, respectively, after LPME extraction of the fluids containing this drug.

I. Separation and Enrichment of Pharmaceuticals from Human Fluids:

(1) Methamphetamine in human plasma and urine with the vial format device: a polypropylene fiber (8.0 cm long, 600 μm inner diameter, 0.2 μm pore size), obtained from Akzo Nobel and sold under the name Accurel PP Q3/2, was connected to a syringe needle (0.81 mm inner diameter) carrying a needle guide head on one end and to a syringe needle of the same dimension without the guide head on the other end. The fiber was dipped into pure 1-octanol contained in a 20 mL glass vial for about 5 seconds. The fiber was then withdrawn and dipped into deionized water contained in a separate 20 mL glass vial and sonicated for 15 seconds. 25 μL of 0.1M hydrochloric acid was injected into the lumen side of the above fiber with a syringe. In the meanwhile, a sample solution was prepared by treating 2.5 mL of the urine or plasma sample containing methamphetamine with 125 μL of 2.0 M sodium hydroxide. The fiber containing the acceptor acid solution was then dipped into this sample solution and the vial was shaken on a Vibramax 100 shaker for 45 minutes. The acceptor solution was then collected into a clean vial by pushing air under pressure from the needle guide head side of the fiber with a syringe and placing a clean microvial at the other end of the fiber. The collected enriched and purified sample in the acceptor solution was then subjected to capillary zone electrophoesis (CZE). Conditions for CZE were 50 mM phosphate (pH 2.75) running buffer, 15 kV separation voltage, 30 cm effective length/75 μm inner diameter capillary tube and UV detection at 200 nm. An extraction efficiency of 75%, together with an enrichment of 75 fold was obtained and the detection limit was 5 ng/mL. The RSD from six experiments was found to be 5.2%. The resulting electropherograms are shown in FIGS. 13-A-B. FIG. 13-A shows an electropherogram for LPME/CZE of 100 ng/ml of methamphine extracted from human urine, while FIG. 13-B shows an electropherogram for LPME/CZE of 100 ng/ml methamphetamine extracted from human plasma.

(2) Naproxen from human urine with the vial format device: a polypropylene fiber, attached to a pair of syringe needles as outlined in example 1, was dipped in hexyl ether for 5 seconds and then sonicated in deionized water for 15 seconds to remove excess hexyl ether adhering to the fiber. Then, 25 μL of a 3:1 mixture of 0.01 M sodium hydroxide/methanol was injected into the lumen side of the fiber. The fiber was dipped into a sample solution consisting of 2.5 μL of urine containing the non-steroidal anti-inflammatory drug naproxen to which 250 μL of 1 M hydrochloric acid has been added. After 45 minutes, the acceptor solution was recovered and subjected to capillary zone electrophoresis with 30 mM acetate (pH 4.75) as running buffer, using a separation voltage of 20 kV, a capillary of 30 cm effective length/75 μm inner diameter and a detection wavelength of 226 nm. An enrichment of 82 fold, along with a recovery of 82% was observed. The RSD from six experiments was 4.6% and the detection limit was 2 ng/mL. The resulting electropherogram is shown in FIG. 14.

(3) Citalopram and its N-desmethyl metabolite from human plasma with the vial format device: a polypropylene fiber, connected to a pair of syringe needles as outlined in example 1, was coated with hexyl ether for 5 seconds and then sonicated in deionized water for 15 seconds to remove excess hexyl ether adhering to the fiber. A 20 mM phosphate buffer solution (pH 2.75, 25 μL) was used as the acceptor solution on the lumen side of the fiber. The fiber was dipped into a mixture of 1 mL of plasma containing 2.73 mL of water and 250 μL of 2 M sodium hydroxide. The plasma sample was obtained from a patient treated with 40 mg of citalopram daily. The recovered acceptor phase after 45 minutes of extraction was analyzed by CZE with 75 mM TRIS-acetic acid (pH 4.6) containing 3% weight/volume of Tween 20 and 75 mg/L of FC-135 as running buffer on a 40 cm capillary column using a detector wavelength of 200 nm. A preconcentration of 30 fold, together with an extraction recovery of 75% could be observed. The RSD from six experiments was 3.6%, with a detection limit of 5 ng/mL. FIG. 15 shows the resulting electropherogram.

Citalopram and methamphetamine in human whole blood employing the vial format device: a polypropylene fiber (280 μm inner diameter, 27 cm length, 0.2 μm pore size and 50 μm wall thickness) was coated with hexyl ether as mentioned in the above examples 2 and 3. The fiber was dipped into 2.5 mL of whole blood containing 1.125 mL water and 125 μL of 2 M sodium hydroxide. Using 17 μL of 0.1 M hydrochloric acid as acceptor, the extraction of the drugs from whole blood was done for 30 minutes. The recovered acceptor solution was analyzed by CZE with 50 mM acetate (pH 4.6) as running buffer, a separation voltage of 15 kV and a detector wavelength of 200 nm on a capillary column of 30 cm effective length. A one hundred fold enrichment of the two drugs was observed. The resulting electropherogram is included in FIG. 16. The upper graph in FIG. 16 corresponds to whole blood containing drugs, while the lower graph corresponds to drug-free whole blood.

Tramadol from human plasma through vial format device: a polypropylene fiber (with dimensions same as in example 4), coated with hexyl ether, was dipped into 0.5 mL of plasma containing 3.25 mL water and 250 μL of 2 M sodium hydroxide for 45 minutes. An acceptor solution of 0.1 M hydrochloric acid (17 μL) was used. Analysis of the enriched acceptor phase was done by CZE with a running buffer consisting of 50 mM phosphate buffer pH 2.5+5 mM carboxymethyl-β-cyclodextrin at 200 nm and 20 kV on a capillary of 50 cm effective length. An enrichment of 30 fold with extraction efficiency of 100% was observed. FIG. 17 shows the resulting electropherogram.

Mianserine from human plasma with a vial format device: a polypropylene fiber of the same dimensions as in example 4 was used in this experiment carried out in the same fashion as described under example 5, except that a running buffer of 75 mM phosphate buffer (pH 3.0)+triethylamine and 2 mM hydroxypropyl-β-cyclodextrin was used. The enrichment was observed to be 15 fold and an extraction efficiency of 50% was registered. The resulting electropherogram is shown in FIG. 18.

Methamphetamine, pethidine, promethazine, methadone and haloperidol from human plasma and whole blood with a vial format device: a polypropylene fiber (8 cm, 600 μm inner diameter, 0.2 μm pore size) suspended in a vial format device was treated with a sample solution comprising of 250 μL of plasma/whole blood, 250 μL of 2.0 M sodium hydroxide and 500 μL of water for 30 minutes. The fiber is coated with hexyl ether membrane and carried 25 μL of 0.01 M hydrochloric acid as acceptor phase. The recovered acceptor solution was subjected to capillary zone electrophoresis with 25 mM phosphate (pH 2.75) as running buffer, 30 kV separation voltage, 200 nm detection wavelength and a 50 cm capillary. Extraction efficiencies of about 55-80% were obtained depending upon the nature/chemistry of the drug, together with enrichment of 6 to 8 fold. The resulting electropherogram is shown in FIG. 19, while Table 5 lists extraction efficiency and enrichment values for the five compounds in plasma and whole blood samples.

TABLE 5

Enrichment of Quinine and Doxepin on Different Liquid Membranes

| | Extraction efficiency/enrichment | |
|---|---|---|
| Compound | Plasma | Whole blood |
| Methamphetamine | 81%/8.1 | 78%/7.8 |
| Pethidine | 74%/7.4 | 72%/7.2 |
| Prometazine | 55%/5.5 | 43%/4.3 |
| Methadone | 64%/6.4 | 54%/5.4 |
| Haloperidol | 67%/6.7 | 55%/5.5 |

Amphetamine from human urine with vial format device: a polypropylene fiber (dimensions, membrane coating and acceptor chemistry as in example 7) was suspended in 2.0 mL of urine containing 250 μL of 2.0 M sodium hydroxide and 2.0 mL of water for 45 minutes with vibration. The resulting acceptor solution was analyzed by capillary electrophoresis under the same conditions described in example 7. Extraction efficiency of 97% and enrichment of 77 was observed. The resulting electropherogram is shown in FIG. 20.

Chlorcyclizine from human plasma with vial format device: a polypropylele fiber (dimensions, membrane coating and acceptor phase as in example 7) was suspended in 2.0 mL of plasma containing 250 μL of 2.0 M sodium hydroxide and 2.0 mL of water for 45 minutes with vibration. The enrichment was 52 and recovery 65%. The resulting electropherogram is shown in FIG. 21.

II. Selectivity Through Acceptor Phase Variation:

A sample solution was prepared by mixing solutions of seven basic drugs containing the drugs at 100 ng/mL concentration (100 μL each) and diluting to 4 mL with water. These drugs consist of amphetamine, methamphetamine, pethidine, chlorcyclizine, methadone, haloperidol and buprenorphine. The pH of the solution was adjusted to be on the basic side by adding 250 μL of 2.0 M sodium hydroxide. A polypropylene hollow fiber was coated with dihexylether to form a supported liquid membrane in the pores of the fiber. The dimensions of the fiber are the same as indicated in Example 1 under Section I. This fiber was dipped into the above seven component drug mix taken in the vial format device and the extraction was allowed to proceed for 60 minutes with shaking by a Vibramax 100 vibrator. The acceptor fluid inside the fiber was 25 μL of the appropriate acid solution listed in Table 1-A. At the conclusion of the extraction period, the acceptor solution was recovered in the manner described under Example 1 (Section I) and subjected to capillary electrophoresis with 25 mM phosphate (pH 2.75) as running buffer, 30 kV separation voltage, 200 nm detector wavelength and a 60 cm capillary column. The results are presented in FIG. 9 and Tables 1-A through 1-C. Recoveries of around 70% could be obtained when hydrochloric, sulphuric and nitric acids and phosphate buffers of pH 1.8 and 2.5 were used as acceptors. On the other hand, with acetic and formic acids as acceptors, the recoveries were in the 40-50% range. Furthermore, enrichment factors of over 120 were recorded with the strong acids and strongly acidic phosphate buffers. The selectivity of different acceptor acids is demonstrated by the fact that for methadone, the enrichment was 138 with hydrochloric acid, while it drops down to 42 with acetate buffer of pH 4.8. On the other hand, for pethidine, the acetate buffer shows an enrichment of 106, while nitric acid shows a figure of 64.

III. Selectivity Through Acceptor Phase pH Variation:

An eight component drug mixture consisting of amphetamine, methamphetamine, pethidine, chlorcyclizine, noscapin, haloperidol, diazepam and reserpine was used. A mixture of 100 μL of each drug (originally at 100 ng/mL concentration) was diluted to 4.0 mL with water and pH of the resulting solution adjusted to the basic side with 2.0 M sodium hydroxide (250 μL). The acceptor solutions were 10 mM phosphate buffers whose pH was adjusted to be 2.5, 3.5, 4.5, 5.5, 6.5 and 7.5, respectively. The fiber dimensions were as described above for example 1. An extraction time of 60 minutes was used. The results of capillary electrophoresis (see FIG. 10 and Tables 2-A-B) show that selective extraction and enrichment of all the eight drugs could be made at lower pH values, while the values drop off starting from pH 5.0.

IV. Selectivity Based on Fiber Chemistry:

The seven-component drug mix described above in Section II was utilized. The extraction experiments were performed on polypropylene fibers of 600 μm inner diameter, 8 cm length and 0.2 μm pore size and on polysulfone fibers of 500 μm inner diameter, 8 cm length and 0.2 μm pore size. Both types of fibers were coated under identical conditions with hexyl ether. Details of sample solution generation are the same as in Section II above. The acceptor solution was 0.01 M hydrochloric acid. FIG. 11 and Tables 3-A-B show the data from these experiments. The selectivity between the fibers is evident from methamphetamine which is enriched to be extent of 82% on polypropylene, while the same drug is recovered to the extent of only 22% on polysulfone. On the other hand, buprenorphine was enriched to the tune of 93% on polysulfone, while the figure for polypropylene is 69%.

V. Selectivity Based on Membrane Chemistry using the Well Format Device:

Four different membrane forming small molecular weight organic liquids were investigated for selectivity differences, viz. hexyl ether, 4-nitrophenyl octyl ether, 1-octanol and 2-octyl-1-dodecanol. The first belongs to an aliphatic ether type, while the second is an aryl alkyl ether containing the polar nitro functionality. The last two are from the aliphatic alcohols variety, but 1-octanol is a straight chain molecule as opposed to the dodecanol which is a branched chain (and longer) molecule. A cover plate of a 96 well block, carrying polypropylene fiber of 8 cm length, 600 μm inner diameter and 0.2 μm pore size, was dipped into each of these pure liquids for 5 seconds. These liquids were contained in different wells of a 96 well plate. The fibers in the cover plate were then washed by sonication in water for 15 seconds to remove excess material sticking to the fibers. A five component mixture of acidic and basic drugs was prepared from acetaminophen, naproxen, bamethane, quinidine and doxepin. Concentrations of the stock drug solutions were 1.0 mg/mL in each case. However, the drugs which have strong absorption in the UV were taken in smaller amounts—20 μL each of acetaminophen, naproxen and doxepin in the mixture, while the other two drugs were taken in larger amounts (100 μL each). This is to maintain roughly the same level of analytical signal with each of these drugs. The mixture was diluted to 20 mL with water so that the concentrations of the three dilute drugs is in the range of 1 μg/mL, while those of the more concentrated drugs is in the range of 5 μg/mL. 500 μL of this diluted mixture of drugs is further diluted eight fold (to 4 mL) with water containing 250 μL of 2.0 M sodium hydroxide and used for extraction. Thus, the concentration of acetaminophen, naproxen and doxepin in the sample solution are about 60 ng and those of quinidine and bamethan are about 300 ng. The acceptor solution consisted of 25 μL of 0.1 M hydrochloric acid in each case. Extraction time with vibration was 30 min for each membrane liquid. The enriched acceptor solution was diluted three fold in each case and 25 μL of the resulting diluted solution used for analysis by high performance liquid chromatography on a Omnisphere C18 column using acetonitrile/pH 7.0 dipotassium hydrogen phosphate as mobile phase. A gradient from 5% acetonitrile to 40% was used to elute the strongly retained components in a reasonable time frame. The results included in Table 4 and FIG. 12 demonstrate over 100 to 200 fold enrichments of the basic drugs quinidine and doxepin. In addition, each of the membrane materials exhibits a different selectivity between quinidine and doxepin. Thus, 1-octanol is selective towards quinidine (2:1 enrichment ratio for quinidine:doxepin), while 2-octyl 1-dodecanol shows a 7:1 enrichment in favor of doxepin. This demonstrates that even within the alcohol group of membranes, depending upon the alkyl chain length one can manipulate selectivity. For nitrophenyl octyl ether, the enrichment ratio doxepin:quinidine works out to 5:1, while for hexyl ether it is 2:1, which again demonstrates the difference in selectivity between aliphatic and aryl-alkyl ethers.

VI. Smaller Sample Volume: Acceptor Volume Ratios:

The sample solution consisted of promethazine, methadone and haloperidol (100 ng each) in 750 μL of water and 250 μL of sodium hydroxide (2.0 M). Hexyl ether is the membrane forming liquid on the polypropylene fiber and the acceptor solution was 0.01 M hydrochloric acid (25 μL). Thus, the sample:acceptor volume ratio is 40:1. The extractions were performed for 2, 5, 10, 15 and 30 minutes, respectively. In a second set of experiments, an acceptor volume of 50 μL was used, so that the sample:acceptor volume ratio becomes 20:1. FIGS. 22-A-C show extraction time profiles for promethazine, methadone, and haloperidol, respectively, for the first set of experiments. FIGS. 22-D-F show extraction time profiles for promethazine, methadone, and haloperidol, respectively, for the second set of experiments. In both sets of experiments, it was found that equilibrium could be reached within 5 min, as illustrated in FIGS. 22-A-F. This example demonstrates that devices and processes according to the present invention can work efficiently with either larger or smaller sample:acceptor volume ratios.

It will be clear to one skilled in the art that the above embodiments may be altered in many ways without departing from the scope of the invention. Although 96 well block formats are presented in the present invention, many other multi-well formats can be applied for the same LPME purpose, such as 48, 24 or 384 well formats etc. Although only one single hollow fiber in each well or vial is pictured in the present formats, multiple hollow fibers can be connected to each of the wells or vial caps. It is understood that any recited steps need not be performed in the exact order listed in a given claim. Accordingly, the scope of the invention should be determined following claims by the and their legal equivalents.

What is claimed is:

1. A sample purification and enrichment method comprising:
   - inserting a donor sample in a well of a multi-well plate, the donor sample comprising an analyte of interest;
   - inserting a tubular hollow porous fiber into the well, the hollow fiber comprising a liquid extraction membrane, the hollow fiber enclosing an internal cavity separated from the donor sample by the liquid extraction membrane;
   - placing a static acceptor liquid in the internal cavity;
   - simultaneously enriching and cleaning up the analyte of interest by extracting the analyte of interest from the donor sample into the acceptor liquid in the internal cavity through the liquid extraction membrane; and
   - transferring the analyte of interest and the acceptor liquid from the internal cavity to an analysis device.

2. The method of claim 1, wherein the multi-well plate is a monolithic plate having fixed wells.

3. The method of claim 1, wherein the multi-well plate comprises a base plate having a plurality of apertures, and a plurality of removable vials each inserted through one of the plurality of apertures, each vial defining a well of the multi-well plate.

4. The method of claim 1, wherein the multi-well plate comprises a bottom block defining the well, and a top fiber-supporting plate mounted on the bottom block, the top plate comprising the fiber, the top plate having a through hole connected to the internal cavity and aligned to the well.

5. The method of claim 4, wherein the top plate further comprises a protective insert extending laterally around the fiber and having an open lower end, for mechanically protecting the fiber.

6. The method of claim 5, wherein the protective insert is tapered such that the open lower end has a smaller size than an upper end of the insert.

7. The method of claim 4, further comprising inserting a guiding pin of the top plate into a corresponding guiding aperture formed in the bottom block around the well, for aligning the fiber in the well, wherein each well of the multi-well plate has at least one individually-corresponding guiding aperture.

8. The method of claim 1, wherein the hollow fiber is a rod-shaped fiber.

9. The method of claim 1, wherein the hollow fiber is a U-shaped fiber.

10. The method of claim 9, wherein the internal cavity is connected to an exterior of the multi-well plate through a single access opening formed in the multi-well plate.

11. The method of claim 9, wherein the internal cavity is connected to an exterior of the multi-well plate through at least two access openings formed in the multi-well plate.

12. The method of claim 1, wherein the hollow fiber comprises two interconnected, parallel longitudinal rods.

13. The method of claim 1, further comprising, after extracting the analyte of interest into the internal cavity, pushing the acceptor liquid and the analyte of interest into an open container corresponding to the well, the container having an inlet connected to the hollow fiber, and an upper outlet opening for allowing the transferring of the analyte of interest and the acceptor liquid from the container to the analysis device.

14. The method of claim 1, further comprising pre-depositing the liquid extraction membrane in the hollow fiber before placing the acceptor liquid in the internal cavity.

15. The method of claim 1, wherein the donor sample has a volume higher than 200 μl and lower than 25 ml.

16. The method of claim 15, wherein the acceptor liquid has a volume higher than 10 μl and lower than 500 μl.

17. The method of claim 15, wherein the acceptor liquid has a volume lower than 100 μl.

18. The method of claim 1, wherein a volume ratio of the donor sample to the acceptor liquid is higher than 20 and lower than 200.

19. The method of claim 1, wherein the hollow fiber has an inner diameter equal or smaller than 1.2 mm and equal or larger than 0.6 mm.

20. The method of claim 19, wherein the hollow fiber is longer than 1 cm and shorter than 20 cm.

21. The method of claim 19, wherein the hollow fiber has an average pore size equal or higher than 0.02 μm and equal or lower than 2 μm.

22. The method of claim 1, wherein the hollow fiber is formed substantially of a material selected from a polymer, a cellulose derivative, a glass fiber, and a ceramic.

23. The method of claim 22 wherein the hollow fiber comprises a material selected from a polyolefin, a polysulfone, polytetrafluoroethylene, a polycarbonate, a polyetherketone, polystyrene, cellulose, cellulose acetate, polysiloxane, polyacrylate, a polyamide, and polyacrylonitrile.

24. The method of claim 22, wherein the sample is an organic sample, and the liquid extraction membrane is an aqueous membrane immiscible with the organic sample.

25. The method of claim 22, wherein the sample is an aqueous sample, and the liquid extraction membrane is an organic membrane immiscible with water.

26. The method of claim 25, wherein the liquid extraction membrane comprises a material selected from an aliphatic hydrocarbon,. an aromatic hydrocarbon, an ether, an ester, a nitrile, an aldehyde, a ketone, and an alcohol.

27. The method of claim 1, wherein different wells of the multi-well plate hold hollow fibers having different chemistries.

28. The method of claim 1, farther comprising analyzing the analyte of interest after transferring the analyte of interest to the analysis device.

29. The method of claim 28, wherein analyzing the analyte of interest comprises performing an analysis selected from a mass spectrometry analysis and a chromatography analysis on the analyte of interest.

30. The method of claim 1, wherein different wells of the multi-well plate hold liquid extraction membranes having different chemistries.

31. The method of claim 1, wherein different wells of the multi-well plate hold acceptor liquids having different pH values.

32. The method of claim 1, wherein different wells of the multi-well plate hold acceptor liquids having different chemistries.

33. A sample purification and enrichment method comprising:
   simultaneously enriching and cleaning up an analyte of interest by extracting the analyte of interest from a donor sample into a static acceptor liquid through a liquid extraction membrane formed in a wall of a porous hollow fiber situated in a well of a multi-well plate, the hollow fiber enclosing the acceptor liquid; and
   transferring the analyte of interest from the hollow fiber to an analysis device.

34. A sample purification and enrichment method comprising:
   simultaneously enriching and cleaning up an analyte of interest by extracting the analyte of interest from a donor sample into a static acceptor liquid through a liquid extraction membrane formed in a porous extraction disk situated in a well of a multi-well plate; and
   transferring the analyte of interest from the well to an analysis device.

35. A hollow-fiber membrane sample preparation multi-well plate for enriching and cleaning up samples, comprising:
   a plurality of wells for holding a corresponding plurality of donor samples, each donor sample comprising an analyte of interest; and
   a plurality of porous hollow fibers situated in the corresponding plurality of wells, each hollow fiber being situated in one of the wells, each hollow fiber including a liquid extraction membrane enclosing an internal cavity of the hollow fiber, for holding a static acceptor liquid within each hollow fiber to receive the analyte of interest through the liquid extraction membrane into the acceptor liquid.

36. The plate of claim 35, wherein the multi-well plate is a monolithic plate having fixed wells.

37. The plate of claim 35, wherein the multi-well plate comprises a base plate having a plurality of apertures, and a plurality of removable vials each inserted through one of the plurality of apertures, each vial defining a well of the plurality of wells.

38. The plate of claim 35, wherein the multi-well plate comprises a bottom block defining the plurality or wells, and a top fiber-supporting plate mounted on the bottom block, the top plate comprising the plurality of fibers, the top plate having an access through hole connected to the internal cavity and aligned to the well.

39. The plate of claim 38, wherein the top plate further comprises a protective insert extending laterally around each fiber and having an open lower end, for mechanically protecting said each fiber.

40. The plate of claim 38, wherein the protective insert is tapered such that the open lower end has a smaller size than an upper end of the insert.

41. The plate of claim 38, wherein the top plate further comprises a plurality of guiding pins, each fiber corresponding individually to at least one of the guiding pins, and wherein the bottom block comprises a plurality of guiding apertures defined between the plurality of wells, each guiding aperture being sized to receive a corresponding guiding pin for aligning the plurality of fibers in the plurality of wells.

42. The plate of claim 35, wherein each hollow fiber is rod-shaped.

43. The plate of claim 35, wherein each hollow fiber is U-shaped.

44. The plate of claim 43, wherein the internal cavity is connected to an exterior of the multi-well plate through a single access opening formed in the multi-well plate.

45. The plate of claim 43, wherein the internal cavity is connected to an exterior of the multi-well plate through at least two access openings formed in the multi-well plate.

46. The plate of claim 35, wherein each hollow fiber comprises two interconnected, parallel longitudinal rods.

47. The plate of claim 35, further comprising a plurality of open collection containers each disposed above one of the wells, each collection container having an inlet connected to the internal cavity, and an upper outlet opening.

48. A hollow-fiber membrane sample preparation plate for enriching and cleaning up samples, comprising:
   a planar top plate having a plurality of access apertures defined therethrough, a spacing of the access apertures being chosen such that each access aperture can be aligned to a well of a sample-holding well block; and
   a plurality of porous hollow fibers hanging from the planar top plate such that each access aperture provides access to an internal cavity defined within one of the fibers, each hollow fiber including a liquid extaction membrane enclosing the internal cavity, for holding a static acceptor liquid within each hollow fiber to receive an analyte of interest from a sample held in the well through the liquid extraction membrane into the acceptor liquid.

49. A sample preparation kit comprising:
   a multi well plate comprising a plurality of wells for holding a corresponding plurality of donor samples each comprising an analyte of interest; and
   a top plate comprising a plurality of porous hollow fibers spaced apart so as to be inserted in the corresponding plurality of wells, each hollow fiber including a liquid extraction membrane for transferring the analyte of interest from the donor solvent to an acceptor liquid through the liquid extraction membrane.

50. A hollow-fiber membrane sample preparation multi-well plate for enriching and cleaning up samples, comprising:
   well means comprising a plurality of wells for holding a corresponding plurality of donor samples, each donor sample comprising an analyte of interest; and hollow fiber support means for holding a plurality of porous hollow fibers in the well means, each hollow fiber being situated in one of the wells, each hollow fiber including a liquid extraction membrane enclosing art internal cavity of the hollow fiber, for holding a static acceptor liquid within each hollow fiber to receive the analyte of interest through the liquid extraction membrane into the acceptor liquid.

* * * * *